United States Patent
Hodge et al.

(10) Patent No.: US 12,227,552 B2
(45) Date of Patent: Feb. 18, 2025

(54) CELL SIGNALING COMPLEXES AND USES THEREOF

(71) Applicant: Nanotein Technologies, Inc., Berkeley, CA (US)

(72) Inventors: Curtis Daniel Hodge, Pinole, CA (US); Zachary Ibrahim Imam, Concord, CA (US); Luke Garland Haines, Pleasant Hill, CA (US)

(73) Assignee: Nanotein Technologies, Inc., Berkeley, CA (US)

( * ) Notice: Subject to any disclaimer, the term of this patent is extended or adjusted under 35 U.S.C. 154(b) by 0 days.

(21) Appl. No.: 18/731,180

(22) Filed: May 31, 2024

(65) Prior Publication Data

US 2025/0011383 A1    Jan. 9, 2025

Related U.S. Application Data

(60) Provisional application No. 63/511,968, filed on Jul. 5, 2023.

(51) Int. Cl.
  *C07K 14/54* (2006.01)
  *C07K 14/55* (2006.01)
  *C12N 5/0783* (2010.01)

(52) U.S. Cl.
  CPC ...... *C07K 14/5443* (2013.01); *C07K 14/5418* (2013.01); *C07K 14/55* (2013.01); *C12N 5/0636* (2013.01); *C07K 2319/02* (2013.01); *C07K 2319/30* (2013.01); *C12N 2501/2302* (2013.01); *C12N 2501/2307* (2013.01); *C12N 2501/2315* (2013.01)

(58) Field of Classification Search
  None
  See application file for complete search history.

(56) References Cited

U.S. PATENT DOCUMENTS

| | | |
|---|---|---|
| 2003/0166877 A1 | 9/2003 | Gillies et al. |
| 2020/0268902 A1* | 8/2020 | Xu ................... C07K 14/54 |
| 2021/0094995 A1 | 4/2021 | Hubbell et al. |
| 2021/0253731 A1 | 8/2021 | Robson et al. |
| 2022/0002383 A1 | 1/2022 | Wong et al. |
| 2022/0143214 A1 | 5/2022 | Deverman et al. |
| 2022/0196655 A1 | 6/2022 | Hodge et al. |
| 2022/0204582 A1 | 6/2022 | Chaudhary |
| 2022/0332800 A1 | 10/2022 | Das et al. |
| 2022/0339193 A1 | 10/2022 | Xiao et al. |
| 2022/0396623 A1 | 12/2022 | Sainson |
| 2023/0174628 A1 | 6/2023 | Xie et al. |

FOREIGN PATENT DOCUMENTS

| | | |
|---|---|---|
| KR | 20130039672 | 4/2013 |
| WO | WO 2000/068248 | 11/2003 |
| WO | WO 2018/172447 | 9/2018 |

OTHER PUBLICATIONS

Benson, H.L. et al. Endogenous matrix metalloproteinases 2 and 9 regulate activation of CD4+ and CD8+ T cells. Am J Respir Cell Mol Biol 44, 700-708 (2011).
Brooks, A.J. et al. Mechanism of activation of protein kinase JAK2 by the growth hormone receptor. Science 344, 1249783 (2014).
De Almeida, L.G.N. et al. Matrix Metalloproteinases: From Molecular Mechanisms to Physiology, Pathophysiology, and Pharmacology. Pharmacol. Rev. 74, 712-768 (2022).
De Taeye, S.W. et al. FcgammaR Binding and ADCC Activity of Human IgG Allotypes. Front. Immunol. 11, 740 (2020).
Edsparr, K., Basse, P.H., Goldfarb, R.H. & Albertsson, P. Matrix metalloproteinases in cytotoxic lymphocytes impact on tumour infiltration and immunomodulation. Cancer Microenviron 4, 351-360 (2011).
Isoda, Y. et al. Importance of the Side Chain at Position 296 of Antibody Fc in Interactions with FcgammaRIIIa and Other Fcgamma Receptors. PLOS One 10, e0140120 (2015).
Johnatty, R.N. et al. Cytokine and chemokine regulation of proMMP-9 and TIMP-1 production by human peripheral blood lymphocytes. J. Immunol. 158, 2327-2333 (1997).
Levin, A.M. et al. Exploiting a natural conformational switch to engineer an interleukin-2 'superkine'. Nature 484, 529-533 (2012).
Liao, W., Lin, J.X. & Leonard, W.J. Interleukin-2 at the crossroads of effector responses, tolerance, and immunotherapy. Immunity 38, 13-25 (2013).
Liu, X. et al. Human immunoglobulin G hinge regulates agonistic anti-CD40 immunostimulatory and antitumour activities through biophysical flexibility. Nature Communications 10, 4206 (2019).
Mayes, P.A., Hance, K.W. & Hoos, A. The promise and challenges of immune agonist antibody development in cancer. Nat. Rev. Drug Discov. 17, 509-527 (2018).
O'Shea, J.J. & Plenge, R. JAK and STAT signaling molecules in immunoregulation and immune-mediated disease. Immunity 36, 542-550 (2012).
Powell, M.S. & Hogarth, P.M. Fc receptors. Adv. Exp. Med. Biol. 640, 22-34 (2008).
Shields, R.L. et al. High resolution mapping of the binding site on human IgG1 for Fc gamma RI, Fc gamma RII, Fc gamma RIII, and FcRn and design of IgG1 variants with improved binding to the Fc gamma R. J. Biol. Chem. 276, 6591-6604 (2001).
Song, J. et al. PROSPER: an integrated feature-based tool for predicting protease substrate cleavage sites. PLOS One 7, e50300 (2012).

(Continued)

*Primary Examiner* — Ilia I Ouspenski
(74) *Attorney, Agent, or Firm* — Levine Bagade Han LLP

(57) ABSTRACT

Disclosed herein are cell signaling complexes such as chimeric cytokine complexes and uses thereof. In some embodiments, a chimeric cytokine complex comprises a protein cage polypeptide, a plurality of engineered Fc antibody domains bound to the protein cage polypeptide, and one or more cytokines linked to each of the plurality of engineered Fc antibody domains. Also disclosed are Fc-cytokine complexes and uses thereof. In some embodiments, an Fc-cytokine complex comprises an engineered Fc antibody domain and one or more cytokines linked to the engineered Fc antibody domain.

27 Claims, 11 Drawing Sheets

Specification includes a Sequence Listing.

(56) References Cited

OTHER PUBLICATIONS

Spangler, J.B., Moraga, I., Mendoza, J.L. & Garcia, K.C. Insights into cytokine-receptor interactions from cytokine engineering. Annu. Rev. Immunol. 33, 139-167 (2015).
Anderson et al., An improved capping unit for stabilizing the ends of the associated β-strands, Department of Chemistry, FEBS Letters 588, 4749-4753 (2014).
Kang et al., Developing an antibody-binding protein cage as a molecular recognition drug modular nanoplatform. Biomaterials, 33, 5423-5430 (2012).
Yen-Ting et al., Structure and Flexibility of Nanoscale Protein Cages Designed by Symmetric Self-Assembly. Journal of the American Chemical Society, 135, 7738-7743 (2013).

* cited by examiner

FIG. 1A Fc-cytokine
FIG. 1B Cytokine-Fc
FIG. 1C Protein Cage Polypeptide
FIG. 1D Cytokine with receptor complex
FIG. 1E Chimeric cytokine complex bound to receptors

Fc-IL-2 (SEQ ID NO: 27)

```
Q Q G N V  C S       N H Y   K S L S L S P G K A P T S S S T
K K    L Q L E    L   D L  M     G     N Y K N P K L      L
```

IL-2-Fc (SEQ ID NO: 28)

```
N   T   D S I       T P K S C D K   H T C P P C P A   L   G P S
V     P P P K P     T L M I S R T P
```

Fc-IL-7 (SEQ ID NO: 29)

```
S R W Q Q G N V   C S       N H Y   K S L S L S P G K D C   I
E G K D G    Y   V     I D L L     M K E I G S N C L N N
```

IL-7-Fc (SEQ ID NO: 30)

```
D L C F L K R    E I K T C W N K I L M G T K E H P K S C D K   T C P
P C P A   L    G P S V   P P P K P     T L M I S R T P E V T C   V V
```

Fc-IL-15 (SEQ ID NO: 31)

```
W Q Q G N V  C S       N H Y   K S L S L S P G K N W V N V I
S   K K I E D L      F I D A   L     E S D V H P S   K V
```

IL-15-Fc (SEQ ID NO: 32)

```
F   T       N T S P K S C D K   H T C P P C P A   L   G P S
V   P P P K P
```

▇ Cleaved by Aspartic protease after this residue (P1 position)

▦ Cleaved by Cysteine protease after this residue (P1 position)

☐ Cleaved by Metalloprotease after this residue (P1 position)

■ Cleaved by Serine protease after this residue (P1 position)

▨ Cleaved by different multiple protease superfamilies after this position (P1 position)

FIG. 3

Engineered Human IgG1 Fc (heavy chain): (SEQ ID NO: 1)

PKSCDKTHT PP PAPELLGGP VFLFPPKPKDTLMISR PEVTCVVVDVS PEVKFNWYVDGVEVHNAK
T E NSTY V SVLTVLHQDWLNGKEYKC VSNK LPAP TIS KGQPREPQVYTLPPSRDELTKN
QVSLTCLVKGFYPS AVEWESNGQPENNYKTTPPVLDSDGSFFLYSKLTVDKSRWQQGNVFSCSVMHEAL
HNHYTQKSLSLSPGK

▨ Cysteine that can form IgG1 disulfide bonds with dimer Fc heavy chain
▨ Site of mutation for modulating FcγR binding
___ Linker regions

FIG. 5

FIG. 9A
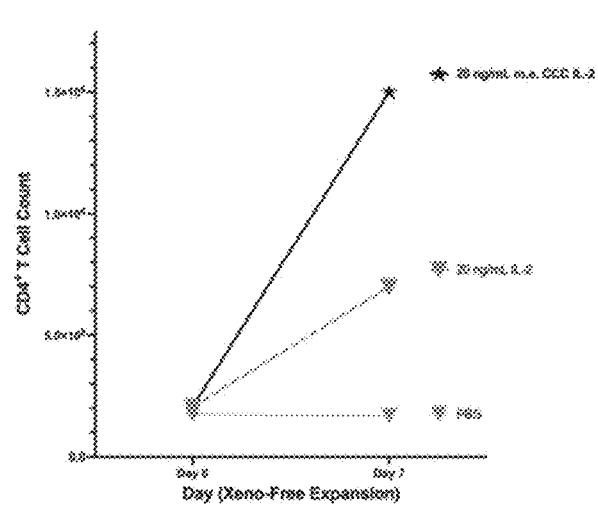
FIG. 9B
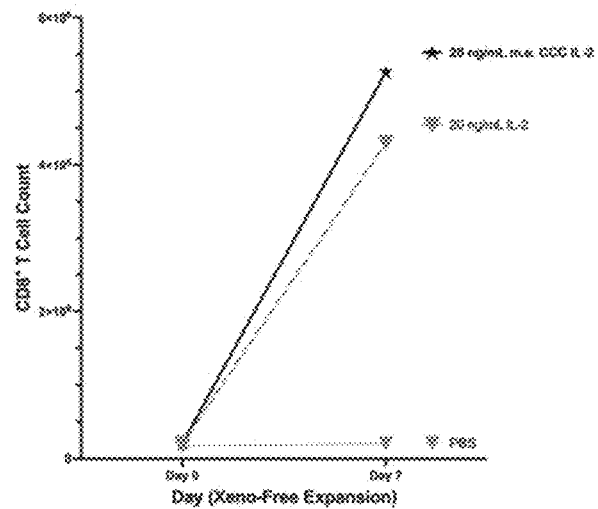
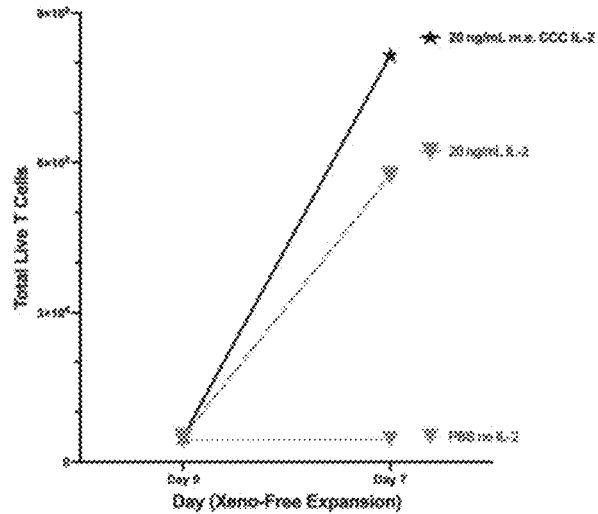
FIG. 9C

CELL SIGNALING COMPLEXES AND USES THEREOF

CROSS-REFERENCE TO RELATED APPLICATION

This application claims priority to U.S. Patent Application No. 63/511,968 filed on Jul. 5, 2023, the content of which is incorporated herein by reference in its entirety.

REFERENCE TO AN ELECTRONIC SEQUENCE LISTING

This application contains a Sequence Listing which has been submitted via Patent Center and is hereby incorporated by reference in its entirety. Said .xml copy, created on May 15, 2024 is named 05_NNTNNZ00100_sequence_listing.xml and is 35,143 bytes in size.

TECHNICAL FIELD

This disclosure relates generally to the field of cell signaling complexes and, more specifically, to cell signaling complexes such as chimeric cytokine complexes and uses thereof.

BACKGROUND

A commonly used mechanism for cellular pathway activation from a cell surface is receptor oligomerization or receptor clustering. For example, receptor oligomerization/clustering is demonstrated through co-stimulatory receptor binding by ligands and agonistic antibodies [1] and by the binding of cell signaling molecules such as cytokines to certain cell receptors [2]. These receptors often include an extracellular domain on the surface of a cell, a transmembrane domain that passes through the cellular membrane, and an intracellular domain on the inside of the cell. In these receptor clustering paradigms, the extracellular domain of the receptors are engaged by cell signaling molecules, which can cause both conformational changes that translate through the membrane to contribute to activation/signaling, and/or oligomerization of multiple receptors that bring together intracellular signaling complexes that drive activation/signaling.

As previously discussed, cytokines are a well-known class of cell signaling proteins. The well-established canonical mechanism for cytokines is the dimerization of extracellular cytokine receptors, often through engagement of two JAK (Janus kinase)-associated receptor subunits in a heterodimeric and sometimes homodimeric fashion [2, 3]. JAK dimerization leads to phosphorylation of STAT (signal transducer and activator of transcription) transcription factors to drive cellular activation through gene regulation [4].

Cytokines can further be classified into interleukins, interferons, chemokines, lymphokines, colony-stimulation factors (CSFs), and tumor necrosis factors (TGFs). One important family of cytokines is the common γ-chain (γc) family of cytokines that play an important role in T cell expansion and survival. Some of the members of the γc family of cytokines include interleukin-2 (IL-2), IL-7, and IL-15.

The functional IL-2-engaged IL-2 receptor signaling complex can consist of sequential binding/complexing of IL-2Rα, IL-2Rβ, and γc subunits as a high-affinity heterotrimer ($K_d \sim 10^{-11}$M) or an ~ 100-fold intermediate affinity dimeric complex of IL-2Rβ, and γc only ($K_d \sim 10^{-9}$M) [2, 5]. IL-2 has a low affinity to the IL-2Rα subunit ($K_d \sim 10^{-8}$M), but this binding does not induce signaling. Naïve T cells are thought to start out with low levels of IL-2Rα, but upon T cell receptor (TCR) activation, IL-2Rα expression is upregulated. IL-2Rβ, and γc are constitutively expressed on lymphohematopoietic cells, which include low-density expression on naïve T cells [5, 6]. In the activated T cell scenario, IL-2 will engage with the upregulated IL-2Rα subunit and the lowly expressed, intermediate affinity IL-2Rβ, and γc heterodimer, leading to low activation in the later or inefficient recruitment of all receptor subunits to assemble the high-affinity signaling complex. Thus, approaches to increase IL-2 receptor signaling could take the form of: (i) increasing the affinity of IL-2 to the signaling-capable IL-2Rβ/γc heterodimer to effectively increase the signaling stability, (ii) increasing the recruitment and assembly of all three IL-2 receptor subunits to form the high-affinity signaling complex, or (iii) increasing the number of productive intermediate and high-affinity signaling complexes on the cell surface.

While there have been successful cytokine engineering efforts aimed at modulating receptor signaling by focusing on modulating IL-2's receptor binding affinity [2, 6], these efforts have focused on direct amino acid changes to the cytokine sequences to disrupt or enhance binding affinities to specific receptor subunits. Such efforts often require labor-intensive and time-intensive techniques such as directed evolution, X-ray crystallography, molecular dynamics simulations, and iterative cytokine-receptor interface engineering [2, 6], while only really taking advantage of the affinity approach. An example of these sequence-based engineering efforts is the development of interleukin-2 (IL-2) variants dubbed "superkines" or super-2s [6].

Therefore, a solution is needed that takes advantage of the various approaches for inducing cytokine receptor signaling described above with respect to increased IL-2 receptor signaling without having to make sequence-based changes to the cytokines themselves. Moreover, such a solution should increase the affinity of cytokines to their signaling receptors while also increasing the overall number of cytokine-receptor signaling complexes per T cell. Furthermore, such a solution should result in increased activation and expansion of human immune cells.

SUMMARY

Disclosed are improved cell signaling complexes capable of facilitating the activation and expansion of immune cells. More specifically, disclosed are cell signaling complexes capable of facilitating the activation and expansion of immune cells (e.g., human donor peripheral blood T cells, human peripheral blood NK cells, etc.).

In some embodiments, a chimeric cytokine complex comprises a protein cage polypeptide, a plurality of engineered Fc antibody domains bound to the protein cage polypeptide, and one or more cytokines linked to each of the plurality of engineered Fc antibody domains.

Also disclosed is a method of activating and expanding immune cells. The method can comprise adding a chimeric cytokine complex to a population of immune cells. The chimeric cytokine complex can comprise a protein cage polypeptide, a plurality of engineered Fc antibody domains bound to the protein cage polypeptide, and one or more cytokines linked to each of the plurality of Fc antibody domains.

In some embodiments, the population of immune cells can be activated and expanded in vitro. In various embodiments, the population of immune cells can be human donor peripheral blood immune cells.

In various embodiments, the population of immune cells can be live T cells.

In various embodiments, the population of immune cells can be natural killer (NK) cells.

In some embodiments, the method can further comprise activating the population of T cells with an anti-CD3 and anti-CD28 T-cell activation reagent prior to adding the chimeric cytokine complex.

In various embodiments, the cytokines can be interleukins. The interleukins can be at least one of interleukin-2s (IL-2s), IL-7s, and IL-15s.

In various embodiments, the plurality of engineered Fc antibody domains can comprise between six and twelve engineered Fc antibody domains bound to the protein cage polypeptide. In some embodiments, between 12 and 24 cytokines can be linked to the plurality of engineered Fc antibody domains in total.

In various embodiments, each of the one or more cytokines can be linked to one of the engineered Fc antibody domains via an engineered metalloprotease-resistant linker sequence. In some embodiments, the engineered metalloprotease-resistant linker sequence can be between 7 to 13 amino acid residues in length.

In various embodiments, at least one of the engineered Fc antibody domains can be C-terminally linked to an N-terminus of at least one of the cytokines.

In some embodiments, one of the cytokines can be interleukin-2 (IL-2) and at least one of the engineered Fc antibody domains can be linked to the IL-2 via an engineered metalloprotease-resistant linker sequence comprising the amino acid sequence SLSPGKAPTS (SEQ ID NO:20).

In some embodiments, one of the cytokines is interleukin-7 (IL-7) and at least one of the engineered Fc antibody domains can be linked to the IL-7 via an engineered metalloprotease-resistant linker sequence comprising the amino acid sequence SLSPGKDCDIEGK (SEQ ID NO:21).

In some embodiments, one of the cytokines can be interleukin-15 (IL-15) and at least one of the engineered Fc antibody domains can be linked to the IL-15 via an engineered metalloprotease-resistant linker sequence comprising the amino acid sequence SLSPGKN (SEQ ID NO:22).

In some embodiments, at least one of the engineered Fc antibody domains can be N-terminally linked to a C-terminus of at least one of the cytokines.

In some embodiments, one of the cytokines can be interleukin-2 (IL-2) and at least one of the engineered Fc antibody domains can be linked to the IL-2 via an engineered metalloprotease-resistant linker sequence comprising the amino acid sequence TPKSCDKTHT (SEQ ID NO:23).

In some embodiments, one of the cytokines can be interleukin-7 (IL-7) and at least one of the engineered Fc antibody domains can be linked to the IL-7 via an engineered metalloprotease-resistant linker sequence comprising the amino acid sequence HPKSCDKTHT (SEQ ID NO:24).

In some embodiments, one of the cytokines can be interleukin-15 (IL-15) and at least one of the engineered Fc antibody domains can be linked to the IL-15 via an engineered metalloprotease-resistant linker sequence comprising the amino acid sequence TSPKSCDKTHT (SEQ ID NO:25).

In various embodiments, the engineered Fc antibody domains can be engineered human Fc antibody domains.

In some embodiments, the engineered human Fc antibody domains can be engineered human IgG1 Fc antibody domains.

In various embodiments, one of the engineered human IgG1 Fc antibody domains can comprise an amino acid sequence with at least about 70%, 75%, 80%, 85%, 90%, 95%, 99%, or 100% amino acid identity to the amino acid sequence set forth in SEQ ID NO:1.

In some embodiments, the engineered human IgG1 Fc antibody domain can comprise at least one of the following point mutations relative to SEQ ID NO: 1 to decrease affinity for certain Fcγ receptors and functionally reduce antibody-dependent cellular cytotoxicity (ADCC): P75L, R76W, Y80K, Y80P, Y80R, Y80G, and Y80A.

In some embodiments, the engineered human IgG1 Fc antibody domain can comprise the following point mutation relative to SEQ ID NO: 1 to increase affinity for certain Fcγ receptors and functionally increase antibody-dependent cellular cytotoxicity (ADCC): Y80W.

In some embodiments, the engineered human IgG1 Fc antibody domain can comprise at least one of the following point mutations relative to SEQ ID NO:1 to decrease affinity for certain Fcγ receptors and have a neutral effect on other Fcγ receptors: S23A, E53A, E77A, Y80F, V87A, A111G, K122A, and D160A.

In some embodiments, the engineered human IgG1 Fc antibody domain can comprise at least one of the following point mutations relative to SEQ ID NO: 1 to increase affinity for certain Fcγ receptors and have a neutral effect on other Fcγ receptors: E117, K118A, and A123T.

In some embodiments, the engineered human IgG1 Fc antibody domain can comprise at least one of the following point mutations relative to SEQ ID NO: 1 to increase affinity for certain Fcγ receptors and decrease affinity for certain other Fcγ receptors: H52A, R85A, and K106A.

In some embodiments, the engineered human IgG1 Fc antibody domain can comprise at least one of the following point mutations relative to SEQ ID NO:1 to decrease affinity for certain Fcγ receptors: D54A, Q79A, and A111S.

In some embodiments, the engineered human IgG1 Fc antibody domain can comprise at least one of the following point mutations relative to SEQ ID NO:1 to increase affinity for certain Fcγ receptors: T40A and K74A.

In some embodiments, the Fc antibody domains can be engineered rabbit Fc antibody domains.

In various embodiments, the chimeric cytokine complex can further comprise a signal peptide linked to an N-terminus of at least one of the engineered Fc antibody domains or at least one of the cytokines.

In some embodiments, the signal peptide can be a murine Ig heavy signal peptide used for expression in Chinese hamster ovary (CHO) cells. In some embodiments, the signal peptide can comprise the amino acid sequence MGWSCIILFLVATATGVHS (SEQ ID NO: 26).

In various embodiments, the protein cage polypeptide can comprise a polypeptide comprising an amino acid sequence with at least about 70%, 75%, 80%, 85%, 90%, 95%, 99%, or 100% amino acid identity to the amino acid sequence set forth in any one of SEQ ID NOS: 8-15.

In some embodiments, the amino acid sequence making up the polypeptide of the protein cage polypeptide can comprise at least the following point mutation relative to the amino acid sequence set forth in any one of SEQ ID NOS: 8-15: Y294A.

In some embodiments, the protein cage polypeptide can comprise a polypeptide comprising a binding site for one of the engineered Fc antibody domains. The binding site can comprise the amino acid sequence RWGSGAD-CAWHLGELVWCTAGSGWE (SEQ ID NO: 16).

In some embodiments, the protein cage polypeptide can comprise a polypeptide comprising a binding site for one of the engineered Fc antibody domains. The binding site can comprise the amino acid sequence GGRWGAD-CAWHLGELVWCTAGWEGG (SEQ ID NO: 17).

In some embodiments, the protein cage polypeptide can comprise a polypeptide comprising a binding site for one of the engineered Fc antibody domains. The binding site can comprise the amino acid sequence GAD-CAWHLGELVWCTAG (SEQ ID NO:18).

In some embodiments, the protein cage polypeptide can comprise a polypeptide comprising a binding site for one of the engineered Fc antibody domains. The binding site can comprise the amino acid sequence RWGSGCD-CAWHLGELVWCTCGSGWE (SEQ ID NO: 19).

In some embodiments, the protein cage polypeptide can self-assemble into a tetrahedral pyramid structure.

In some embodiments, an Fc-cytokine complex is disclosed comprising an engineered Fc antibody domain and one or more cytokines linked to the engineered Fc antibody domain.

Also disclosed is a method of activating and expanding immune cells using the Fc-cytokine complex. The method can comprise adding an Fc-cytokine complex to a population of immune cells. The Fc-cytokine complex can comprise an Fc antibody domain and one or more cytokines linked to the Fc antibody domain.

In some embodiments, the population of immune cells can be activated and expanded in vitro. In various embodiments, the population of immune cells can be human donor peripheral blood immune cells. In various embodiments, the population of immune cells can be live T cells.

In some embodiments, the population of immune cells can be natural killer (NK) cells.

In some embodiments, the method can further comprise activating the population of T cells with an anti-CD3 and anti-CD28 T-cell activation reagent prior to adding the Fc-cytokine complex.

In various embodiments, the cytokines can be interleukins.

In some embodiments, the interleukins can be at least one of interleukin-2s (IL-2s), IL-7s, and IL-15s.

In various embodiments, each of the one or more cytokines can be linked to the engineered Fc antibody domain via an engineered metalloprotease-resistant linker sequence. In some embodiments, the engineered metalloprotease-resistant linker sequence can be between 7 to 13 amino acid residues in length.

In various embodiments, the engineered Fc antibody domain can be C-terminally linked to an N-terminus of at least one of the cytokines.

In some embodiments, one of the cytokines can be interleukin-2 (IL-2) and the engineered Fc antibody domain can be linked to the IL-2 via an engineered metalloprotease-resistant linker sequence comprising the amino acid sequence SLSPGKAPTS (SEQ ID NO: 20).

In some embodiments, one of the cytokines can be interleukin-7 (IL-7) and the engineered Fc antibody domain can be linked to the IL-7 via an engineered metalloprotease-resistant linker sequence comprising the amino acid sequence SLSPGKDCDIEGK (SEQ ID NO: 21).

In some embodiments, one of the cytokines can be interleukin-15 (IL-15) and the engineered Fc antibody domain can be linked to the IL-15 via an engineered metalloprotease-resistant linker sequence comprising the amino acid sequence SLSPGKN (SEQ ID NO:22).

In various embodiments, the engineered Fc antibody domain can be N-terminally linked to a C-terminus of at least one of the cytokines.

In some embodiments, one of the cytokines can be interleukin-2 (IL-2) and the engineered Fc antibody domain can be linked to the IL-2 via an engineered metalloprotease-resistant linker sequence comprising the amino acid sequence TPKSCDKTHT (SEQ ID NO: 23).

In some embodiments, one of the cytokines can be interleukin-7 (IL-7) and the engineered Fc antibody domain can be linked to the IL-7 via an engineered metalloprotease-resistant linker sequence comprising the amino acid sequence HPKSCDKTHT (SEQ ID NO: 24).

In some embodiments, one of the cytokines can be interleukin-15 (IL-15) and the engineered Fc antibody domain can be linked to the IL-15 via an engineered metalloprotease-resistant linker sequence comprising the amino acid sequence TSPKSCDKTHT (SEQ ID NO: 25).

In various embodiments, the engineered Fc antibody domain can be an engineered human Fc antibody domain. In some embodiments, the engineered human Fc antibody domain can be an engineered human IgG1 Fc antibody domain.

In some embodiments, the engineered human IgG1 Fc antibody domain can comprise an amino acid sequence with at least about 70%, 75%, 80%, 85%, 90%, 95%, 99%, or 100% amino acid identity to the amino acid sequence set forth in SEQ ID NO:1.

In some embodiments, the engineered human IgG1 Fc antibody domain can comprise at least one of the following point mutations relative to SEQ ID NO: 1 to decrease affinity for certain Fcγ receptors and functionally reduce antibody-dependent cellular cytotoxicity (ADCC): P75L, R76W, Y80K, Y80P, Y80R, Y80G, and Y80A.

In some embodiments, the engineered human IgG1 Fc antibody domain can comprise the following point mutation relative to SEQ ID NO: 1 to increase affinity for certain Fcγ receptors and functionally increase antibody-dependent cellular cytotoxicity (ADCC): Y80W.

In some embodiments, the engineered human IgG1 Fc antibody domain can comprise at least one of the following point mutations relative to SEQ ID NO: 1 to decrease affinity for certain Fcγ receptors and have a neutral effect on other Fcγ receptors: S23A, E53A, E77A, Y80F, V87A, A111G, K122A, and D160A.

In some embodiments, the engineered human IgG1 Fc antibody domain can comprise at least one of the following point mutations relative to SEQ ID NO: 1 to increase affinity for certain Fcγ receptors and have a neutral effect on other Fcγ receptors: E117, K118A, and A123T.

In some embodiments, the engineered human IgG1 Fc antibody domain can comprise at least one of the following point mutations relative to SEQ ID NO:1 to increase affinity for certain Fcγ receptors and decrease affinity for certain other Fcγ receptors: H52A, R85A, and K106A.

In some embodiments, the engineered human IgG1 Fc antibody domain can comprise at least one of the following point mutations relative to SEQ ID NO: 1 to decrease affinity for certain Fcγ receptors: D54A, Q79A, and A111S.

In some embodiments, the engineered human IgG1 Fc antibody domain can comprise at least one of the following point mutations relative to SEQ ID NO:1 to increase affinity for certain Fcγ receptors: T40A and K74A.

In some embodiments, the Fc antibody domain can be an engineered rabbit Fc antibody domain.

In various embodiments, the Fc-cytokine complex can further comprise a signal peptide linked to an N-terminus of the engineered Fc antibody domain or at least one of the cytokines. In some embodiments, the signal peptide can be a murine Ig heavy signal peptide used for expression in Chinese hamster ovary (CHO) cells. In some embodiments, the signal peptide can comprise the amino acid sequence MGWSCIILFLVATATGVHS (SEQ ID NO: 26).

BRIEF DESCRIPTION OF THE DRAWINGS

FIG. 3 illustrates example linker sequences designed to link the Fc and cytokine components of various CCCs.

FIG. 5 illustrates that the Fc component of the CCC can be engineered through mutation of key sites in its FcγR-binding portion.

FIGS. 9A-9C are graphs illustrating the CD4+ T cell count, the CD8+ T cell count, and the total live T cells at day 7, respectively, of T cells activated and expanded by CCCs and cytokines alone. A phosphate buffered saline (PBS) solution was used as the control.

DETAILED DESCRIPTION

Figure 1:
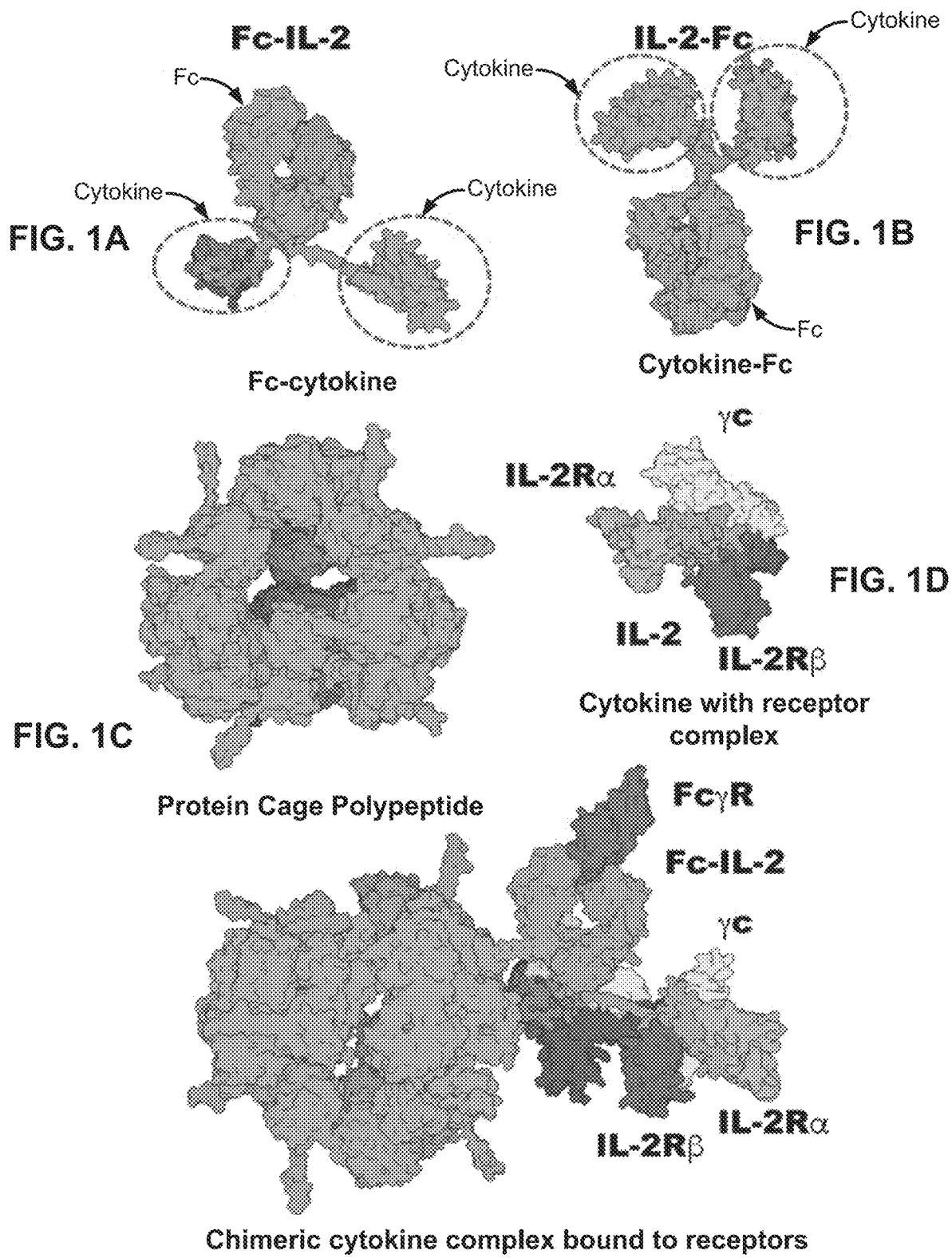
FIGS. 1A and 1B illustrate predicted structures that represent one embodiment of an engineered Fc antibody domain linked to a plurality of cytokines.
FIG. 1C illustrates a predicted structure of one embodiment of an engineered self-assembling protein cage polypeptide.
FIG. 1D illustrates a predicted structure of one embodiment of a cytokine (e.g., IL-2) and its receptor signaling complex.
FIG. 1E illustrates a predicted structure of one embodiment of a chimeric cytokine complex (CCC) comprising an Fc-cytokine bound to an engineered self-assembling protein cage polypeptide and a receptor signaling complex bound to the cytokine of the CCC.

FIGS. 1A and 1B illustrate predicted structures that represent one embodiment of an engineered Fc antibody domain linked to a plurality of cytokines. For example, FIG. 1A illustrates a predicted structure of an engineered Fc antibody domain (e.g., an engineered IgG1 Fc heavy chain) C-terminally linked to two IL-2 cytokines. Also, for example, FIG. 1B illustrates a predicted structure of an engineered Fc antibody domain (e.g., an engineered IgG1 Fc heavy chain) N-terminally linked to two IL-2 cytokines.

In some embodiments, the engineered Fc antibody domain can be an engineered human Fc antibody domain. For example, the Fc antibody domain can be an engineered human IgG1 Fc antibody domain.

In some embodiments, the engineered human IgG1 Fc antibody domain can comprise an amino acid sequence with at least about 70%, 75%, 80%, 85%, 90%, 95%, 99%, or 100% amino acid identity to the amino acid sequence set forth in SEQ ID NO:1 (see Table 1).

In other embodiments, the Fc antibody domain can be an engineered rabbit Fc antibody domain. For example, the Fc antibody domain can be an engineered rabbit IgG Fc antibody domain.

Although FIGS. 1A and 1B illustrate the cytokines as IL-2s, it is contemplated by this disclosure that other interleukins such as IL-7s and IL-15s (see, e.g., FIGS. 3 and 6) can also act as the cytokines. Moreover, it is contemplated by this disclosure that other receptor-engaging molecules (engineered or natural) can be used as the cell signaling component of the CCCs.

FIG. 1C illustrates a predicted structure of an engineered self-assembling protein cage polypeptide. As shown in FIG. 1C, the protein cage polypeptide can self-assemble into a tetrahedral pyramid structure. The protein cage polypeptide can also self-assemble into a compact asymmetrical multimeric structure or a cage-cage multimer (including dimers).

The protein cage polypeptide can be any of the protein cage polypeptides or scaffolding proteins discussed in U.S. Patent Publication No. 2022/0196655, the content of which is incorporated herein by reference in its entirety.

The engineered self-assembling protein cage polypeptide can serve as a carrier or scaffold for a plurality of engineered Fc antibody domains, each linked to one or more cytokines. When the plurality of engineered Fc antibody domains (each linked to one or more cytokines) are bound to the protein cage polypeptide, such a structure is referred to herein as a chimeric cytokine complex (CCC).

FIG. 1D illustrates an example of a cytokine (e.g., IL-2) and its receptor signaling complex. In some embodiments, the receptor signaling complex can comprise IL-2Rα, IL-2Rβ, and γc. In other embodiments, the receptor complex can be the dimeric complex of IL-2Rβ, and γc only.

FIG. 1E illustrates a predicted structure of an example CCC comprising an Fc-cytokine bound to an engineered self-assembling protein cage polypeptide and a receptor signaling complex bound to the cytokine of the CCC (e.g., IL-2). The protein cage polypeptide can comprise a plurality of potential binding sites for the engineered Fc antibody domains. For example, the protein cage polypeptide can comprise up to 12 binding sites for Fc antibody domains.

Although FIG. 1E illustrates only one Fc-cytokine chimera (e.g., Fc-IL-2) bound to the protein cage polypeptide, it is contemplated by this disclosure that between six and twelve engineered Fc antibody domains can be bound to one protein cage polypeptide.

Since each engineered Fc antibody domain can comprise up to two cytokines, each CCC can comprise between 12 and 24 cytokines.

TABLE 1

Engineered Fc sequence and engineered Fc-cytokine sequences designed and experimentally tested to-date.

| SEQ ID NO: | NAME | SEQUENCE |
|---|---|---|
| 1 | Engineered Human IgG1 Fc | PKSCDKTHTCPPCPAPELLGGPSVFLFPPKPKDTLMISRTPE VTCVVVDVSHEDPEVKFNWYVDGVEVHNAKTKPREEQY NSTYRVVSVLTVLHQDWLNGKEYKCKVSNKALPAPIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 2 | Engineered Fc-IL-2 | MGWSCIILFLVATATGVHSPKSCDKTHTCPPCPAPELLGGP SVFLFPPKPKDTLMISRTPEVTCVVVDVSHEDPEVKENWY VDGVEVHNAKTKPREEQYNSTYRVVSVLTVLHQDWLNG KEYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHY TQKSLSLSPGKAPTSSSTKKTQLQLEHLLLDLQMILNGINN YKNPKLTRMLTFKFYMPKKATELKHLQCLEEELKPLEEV LNLAQSKNFHLRPRDLISNINVIVLELKGSETTFMCEYADE TATIVEFLNRWITFCQSIISTLT |
| 3 | Engineered IL-2-Fc | MGWSCIILFLVATATGVHSAPTSSSTKKTQLQLEHLLLDL QMILNGINNYKNPKLTRMLTFKFYMPKKATELKHLQCLE EELKPLEEVLNLAQSKNFHLRPRDLISNINVIVLELKGSETT FMCEYADETATIVEFLNRWITFCQSIISTLTPKSCDKTHTCP PCPAPELLGGPSVFLFPPKPKDTLMISRTPEVTCVVVDVSH EDPEVKFNWYVDGVEVHNAKTKPREEQYNSTYRVVSVL TVLHQDWLNGKEYKCKVSNKALPAPIEKTISKAKGQPREP QVYTLPPSRDELTKNQVSLTCLVKGFYPSDIAVEWESNGQ PENNYKTTPPVLDSDGSFFLYSKLTVDKSRWQQGNVFSCS VMHEALHNHYTQKSLSLSPGK |
| 4 | Engineered Fc-IL-7 | MGWSCIILFLVATATGVHSPKSCDKTHTCPPCPAPELLGGP SVFLFPPKPKDTLMISRTPEVTCVVVDVSHEDPEVKFNWY VDGVEVHNAKTKPREEQYNSTYRVVSVLTVLHQDWLNG KEYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHY TQKSLSLSPGKDCDIEGKDGKQYESVLMVSIDQLLDSMKE IGSNCLNNEFNFFKRHICDANKEGMFLFRAARKLRQFLKM NSTGDFDLHLLKVSEGTTILLNCTGQVKGRKPAALGEAQP TKSLEENKSLKEQKKLNDLCFLKRLLQEIKTCWNKILMGT KEH |
| 5 | Engineered IL-7-Fc | MGWSCIILFLVATATGVHSDCDIEGKDGKQYESVLMVSID QLLDSMKEIGSNCLNNEFNFFKRHICDANKEGMFLFRAAR KLRQFLKMNSTGDFDLHLLKVSEGTTILLNCTGQVKGRKP AALGEAQPTKSLEENKSLKEQKKLNDLCFLKRLLQEIKTC WNKILMGTKEHPKSCDKTHTCPPCPAPELLGGPSVFLFPP KPKDTLMISRTPEVTCVVVDVSHEDPEVKFNWYVDGVEV HNAKTKPREEQYNSTYRVVSVLTVLHQDWLNGKEYKCK VSNKALPAPIEKTISKAKGQPREPQVYTLPPSRDELTKNQV SLTCLVKGFYPSDIAVEWESNGQPENNYKTTPPVLDSDGS FFLYSKLTVDKSRWQQGNVFSCSVMHEALHNHYTQKSLS LSPGK |
| 6 | Engineered Fc-IL-15 | MGWSCIILFLVATATGVHSPKSCDKTHTCPPCPAPELLGGP SVFLFPPKPKDTLMISRTPEVTCVVVDVSHEDPEVKFNWY VDGVEVHNAKTKPREEQYNSTYRVVSVLTVLHQDWLNG KEYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHY TQKSLSLSPGKNWVNVISDLKKIEDLIQSMHIDATLYTESD VHPSCKVTAMKCFLLELQVISLESGDASIHDTVENLIILAN NSLSSNGNVTESGCKECEELEEKNIKEFLQSFVHIVQMFIN TS |
| 7 | Engineered IL-15-Fc | MGWSCIILFLVATATGVHSNWVNVISDLKKIEDLIQSMHI DATLYTESDVHPSCKVTAMKCFLLELQVISLESGDASIHD TVENLIILANNSLSSNGNVTESGCKECEELEEKNIKEFLQSF VH The protein cage polypeptide of the CCC can comprise a polypeptide of between about 400 and about 700 amino acid residues in length. In some embodiments, the protein cage polypeptide can comprise a polypeptide of about 450 to about 650 amino acid residues in length.

In some embodiments, the protein cage polypeptide can be comprised of a polypeptide comprising an amino acid sequence with at least about 70%, 75%, 80%, 85%, 90%, 95%, 99%, or 100% amino acid identity to the amino acid sequence set forth in any one of SEQ ID NOS: 8-11 (see Table 2).

The protein cage polypeptide set forth in SEQ ID NO. 12 can be designed by the applicant to be a Y294A mutant of the protein cage polypeptide set forth in SEQ ID NO. 8 (see Table 2). The protein cage polypeptide set forth in SEQ ID NO. 13 can be designed by the applicant to be a Y294A mutant of the protein cage polypeptide set forth in SEQ ID NO. 9 (see Table 2). The protein cage polypeptide set forth in SEQ ID NO. 14 can be designed by the applicant to be a Y294A mutant of the protein cage polypeptide set forth in SEQ ID NO. 10 (see Table 2). The protein cage polypeptide set forth in SEQ ID NO. 15 can be designed by the applicant to be a Y294A mutant of the protein cage polypeptide set forth in SEQ ID NO:11 (see Table 2).

The various protein cage polypeptides disclosed herein can also comprise peptide sequences capable of binding to the engineered Fc antibody domain. For example, the protein cage polypeptides set forth in SEQ ID NOS: 8 and 12 can comprise the amino acid sequence RWGSGADCAWHLGELVWCTAGSGWE (SEQ ID NO:16) (referred to herein as Peptide Sequence A, see Table 2) for binding to the engineered Fc antibody domain.

In addition, the protein cage polypeptides set forth in SEQ ID NOS: 9 and 13 can comprise the amino acid sequence GGRWGADCAWHLGELVWCTAGWEGG (SEQ ID NO: 17) (referred to herein as Peptide Sequence B, see Table 2) for binding to the engineered Fc antibody domain.

Moreover, the protein cage polypeptides set forth in SEQ ID NOS: 10 and 14 can comprise the amino acid sequence GADCAWHLGELVWCTAG (SEQ ID NO:18) (referred to herein as Peptide Sequence C, see Table 2) for binding to the engineered Fc antibody domain.

Furthermore, the protein cage polypeptides set forth in SEQ ID NOS: 11 and 15 can comprise the amino acid sequence RWGSGCDCAWHLGELVWCTCGSGWE (SEQ ID NO: 19) (referred to herein as Peptide Sequence D, see Table 2) for binding to the engineered Fc antibody domain.

TABLE 2

Sequences of protein cage polypeptide variants designed and experimentally tested to-date and peptide sequences capable of binding to the engineered Fc antibody domain.

| SEQ ID NO: | NAME | SEQUENCE |
| --- | --- | --- |
| 8 | Protein cage polypeptide 1 | MPFITVGQENSTSIDLYYEDHGTGTPVVLIHGFPLSGHSWERQSAALLDAGYRVITYDRRGFGQSSQPTTGYDYDTFAADLNTVLETLDLQDAVLVGFSMGTGEVARYVSSYGTARIAAVAFLASLEPFLLKTDDNPDGAAPQEFFDGIVAAVKADRYAFYTGFFNDFYNLDENLGTRISEEAVRNSWNTAASGGFFAAAAAPTTWYTDFRADIPRIDVPALILHGTGDRTLPIENTARVFHKALPSAEYVEVEGAPHGLLWTHAEEVNTALLAFLAKAQEAQKQKLLTEVETYVLSIIPSGPLKAEIAQRLEDVFAGRWGSGADCAWHLGELVWCTAGSGWEDLEVLMEWLKTRPILSPLTKGILGFVFTLTVPSERGLQRRRFVQNALNGNGDPNNMDKAVKLYRKLKREITFHGAKEISLSYSAGALASCMGLIYNRMGAVTTEVAFGLVCATCEQIADSQHRSHRQLEHHHHHH |
| 9 | Protein cage polypeptide 2 | MPFITVGQENSTSIDLYYEDHGTGTPVVLIHGFPLSGHSWERQSAALLDAGYRVITYDRRGFGQSSQPTTGYDYDTFAADLNTVLETLDLQDAVLVGFSMGTGEVARYVSSYGTARIAAVAFLASLEPFLLKTDDNPDGAAPQEFFDGIVAAVKADRYAFYTGFFNDFYNLDENLGTRISEEAVRNSWNTAASGGFFAAAAAPTTWYTDFRADIPRIDVPALILHGTGDRTLPIENTARVFHKALPSAEYVEVEGAPHGLLWTHAEEVNTALLAFLAKAQEAQKQKLLTEVETYVLSIIPSGPLKAEIAQRLEDVFAGGGRWGADCAWHLGELVWCTAGWEGGDLEVLMEWLKTRPILSPLTKGILGFVFTLTVPSERGLQRRRFVQNALNGNGDPNNMDKAVKLYRKLKREITFHGAKEISLSYSAGALASCMGLIYNRMGAVTTEVAFGLVCATCEQIADSQHRSHRQLEHHHHHH |
| 10 | Protein cage polypeptide 3 | MPFITVGQENSTSIDLYYEDHGTGTPVVLIHGFPLSGHSWERQSAALLDAGYRVITYDRRGFGQSSQPTTGYDYDTFAADLNTVLETLDLQDAVLVGFSMGTGEVARYVSSYGTARIAAVAFLASLEPFLLKTDDNPDGAAPQEFFDGIVAAVKADRYAFYTGFFNDFYNLDENLGTRISEEAVRNSWNTAASGGFFAAAAAPTTWYTDFRADIPRIDVPALILHGTGDRTLPIENTARVFHKALPSAEYVEVEGAPHGLLWTHAEEVNTALLAFLAKAQEAQKQKLLTEVETYVLSIIPSGPLKAEIAQRLEDVFAGGADCAWHLGELVWCTAGDLEVLMEWLKTRPILSPLTKGILGFVFTLTVPSERGLQRRRFVQNALNGNGDPNNMDKAVKLYRKLKREITFHGAKEISLSYSAGALASCMGLIYNRMGAVTTEVAFGLVCATCEQIADSQHRSHRQLEHHHHHH |

TABLE 2-continued

Sequences of protein cage polypeptide variants designed and experimentally tested to-date and peptide sequences capable of binding to the engineered Fc antibody domain.

| SEQ ID NO: | NAME | SEQUENCE |
|---|---|---|
| 11 | Protein cage polypeptide 4 | MPFITVGQENSTSIDLYYEDHGTGTPVVLIHGFPLSGHSWE RQSAALLDAGYRVITYDRRGFGQSSQPTTGYDYDTFAAD LNTVLETLDLQDAVLVGFSMGTGEVARYVSSYGTARIAA VAFLASLEPFLLKTDDNPDGAAPQEFFDGIVAAVKADRYA FYTGFFNDFYNLDENLGTRISEEAVRNSWNTAASGGFFAA AAAPTTWYTDFRADIPRIDVPALILHGTGDRTLPIENTARV FHKALPSAEYVEVEGAPHGLLWTHAEEVNTALLAFLAKA QEAQKQKLLTEVETYVLSIIPSGPLKAEIAQRLEDVFAGR WGSGCDCAWHLGELVWCTCGSGWEDLEVLMEWLKTRPI LSPLTKGILGFVFTLTVPSERGLQRRRFVQNALNGNGDPN NMDKAVKLYRKLKREITFHGAKEISLSYSAGALASCMGLI YNRMGAVTTEVAFGLVCATCEQIADSQHRSHRQLEHHHH HH |
| 12 | Protein cage polypeptide 5 | MPFITVGQENSTSIDLYYEDHGTGTPVVLIHGFPLSGHSWE RQSAALLDAGYRVITYDRRGFGQSSQPTTGYDYDTFAAD LNTVLETLDLQDAVLVGFSMGTGEVARYVSSYGTARIAA VAFLASLEPFLLKTDDNPDGAAPQEFFDGIVAAVKADRYA FYTGFFNDFYNLDENLGTRISEEAVRNSWNTAASGGFFAA AAAPTTWYTDFRADIPRIDVPALILHGTGDRTLPIENTARV FHKALPSAEYVEVEGAPHGLLWTHAEEVNTALLAFLAKA QEAQKQKLLTEVETAVLSIIPSGPLKAEIAQRLEDVFAGR WGSGADCAWHLGELVWCTAGSGWEDLEVLMEWLKTRP ILSPLTKGILGFVFTLTVPSERGLQRRRFVQNALNGNGDPN NMDKAVKLYRKLKREITFHGAKEISLSYSAGALASCMGLI YNRMGAVTTEVAFGLVCATCEQIADSQHRSHRQLEHHHH HH |
| 13 | Protein cage polypeptide 6 | MPFITVGQENSTSIDLYYEDHGTGTPVVLIHGFPLSGHSWE RQSAALLDAGYRVITYDRRGFGQSSQPTTGYDYDTFAAD LNTVLETLDLQDAVLVGFSMGTGEVARYVSSYGTARIAA VAFLASLEPFLLKTDDNPDGAAPQEFFDGIVAAVKADRYA FYTGFFNDFYNLDENLGTRISEEAVRNSWNTAASGGFFAA AAAPTTWYTDFRADIPRIDVPALILHGTGDRTLPIENTARV FHKALPSAEYVEVEGAPHGLLWTHAEEVNTALLAFLAKA QEAQKQKLLTEVETAVLSIIPSGPLKAEIAQRLEDVFAGGG RWGADCAWHLGELVWCTAGWEGGDLEVLMEWLKTRPI LSPLTKGILGFVFTLTVPSERGLQRRRFVQNALNGNGDPN NMDKAVKLYRKLKREITFHGAKEISLSYSAGALASCMGLI YNRMGAVTTEVAFGLVCATCEQIADSQHRSHRQLEHHHH HH |
| 14 | Protein cage polypeptide 7 | MPFITVGQENSTSIDLYYEDHGTGTPVVLIHGFPLSGHSWE RQSAALLDAGYRVITYDRRGFGQSSQPTTGYDYDTFAAD LNTVLETLDLQDAVLVGFSMGTGEVARYVSSYGTARIAA VAFLASLEPFLLKTDDNPDGAAPQEFFDGIVAAVKADRYA FYTGFFNDFYNLDENLGTRISEEAVRNSWNTAASGGFFAA AAAPTTWYTDFRADIPRIDVPALILHGTGDRTLPIENTARV FHKALPSAEYVEVEGAPHGLLWTHAEEVNTALLAFLAKA QEAQKQKLLTEVETAVLSIIPSGPLKAEIAQRLEDVFAGGA DCAWHLGELVWCTAGDLEVLMEWLKTRPILSPLTKGILG FVFTLTVPSERGLQRRRFVQNALNGNGDPNNMDKAVKLY RKLKREITFHGAKEISLSYSAGALASCMGLIYNRMGAVTT EVAFGLVCATCEQIADSQHRSHRQLEHHHHHH |
| 15 | Protein cage polypeptide 8 | MPFITVGQENSTSIDLYYEDHGTGTPVVLIHGFPLSGHSWE RQSAALLDAGYRVITYDRRGFGQSSQPTTGYDYDTFAAD LNTVLETLDLQDAVLVGFSMGTGEVARYVSSYGTARIAA VAFLASLEPFLLKTDDNPDGAAPQEFFDGIVAAVKADRYA FYTGFFNDFYNLDENLGTRISEEAVRNSWNTAASGGFFAA AAAPTTWYTDFRADIPRIDVPALILHGTGDRTLPIENTARV FHKALPSAEYVEVEGAPHGLLWTHAEEVNTALLAFLAKA QEAQKQKLLTEVETAVLSIIPSGPLKAEIAQRLEDVFAGR WGSGCDCAWHLGELVWCTCGSGWEDLEVLMEWLKTRPI LSPLTKGILGFVFTLTVPSERGLQRRRFVQNALNGNGDPN NMDKAVKLYRKLKREITFHGAKEISLSYSAGALASCMGLI YNRMGAVTTEVAFGLVCATCEQIADSQHRSHRQLEHHHH HH |

TABLE 2-continued

Sequences of protein cage polypeptide variants designed and experimentally tested to-date and peptide sequences capable of binding to the engineered Fc antibody domain.

| SEQ ID NO: | NAME | SEQUENCE |
|---|---|---|
| 16 | Peptide sequence A, capable of binding to the engineered Fc antibody domain | RWGSGADCAWHLGELVWCTAGSGWE |
| 17 | Peptide sequence B, capable of binding to the engineered Fc antibody domain | GGRWGADCAWHLGELVWCTAGWEGG |
| 18 | Peptide sequence C, capable of binding to the engineered Fc antibody domain | GADCAWHLGELVWCTAG |
| 19 | Peptide sequence D, capable of binding to the engineered Fc antibody domain | RWGSGCDCAWHLGELVWCTCGSGWE |

Figure 2:
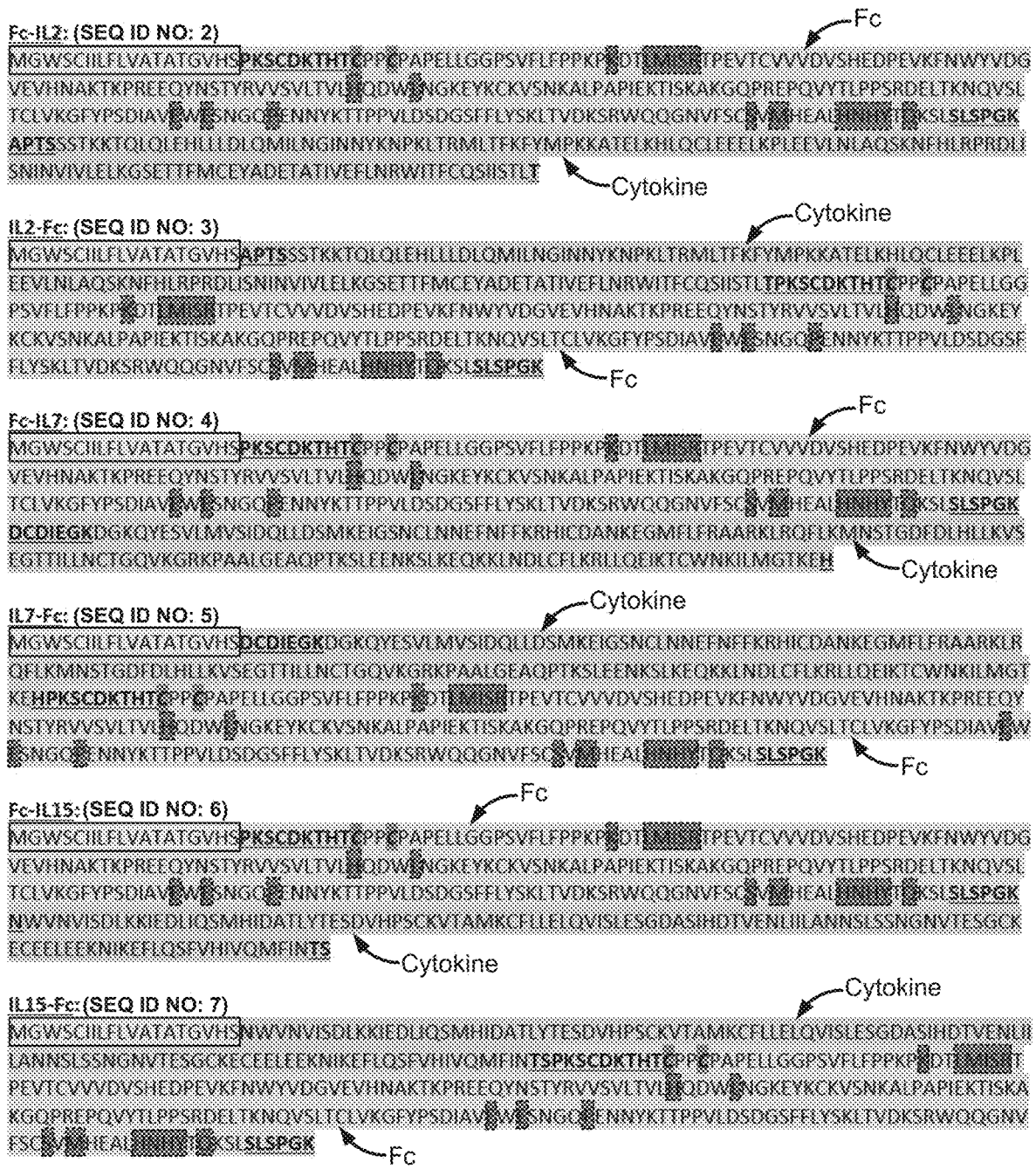
FIG. 2 illustrates that the engineered Fc antibody domains can be C-terminally linked or N-terminally linked to the cytokines to achieve their augmented function of activating and expanding T cells.

FIG. 2 illustrates that the engineered Fc antibody domains can be C-terminally linked or N-terminally linked to the cytokines (the Fc-cytokines can then be bound to a protein cage polypeptide) to achieve their augmented function of activating and expanding T cells beyond the capabilities of soluble cytokines alone. Although the applicant anticipates that C-terminally linked Fc-cytokines facilitate less sterically-restricted FcγR binding, one unexpected discovery made by the applicant is that N-terminally linked Fc-cytokine CCCs also work well to activate and expand T cells beyond the capabilities of soluble cytokines.

As shown in FIG. 2, the engineered Fc antibody domains of the CCCs can be C-terminally linked to an N-terminus of at least one of the cytokines. Table 1 lists out representative sequences for several Fc-cytokine variants.

For example, when one of the cytokines is interleukin-2 (IL-2), at least one of the engineered Fc antibody domains can be C-terminally linked to the N-terminus of the IL-2 (herein referred to as Fc-IL-2) via an engineered metalloprotease-resistant linker sequence. In some embodiments, the engineered metalloprotease-resistant linker sequence can comprise the amino acid sequence SLSPGKAPTS (SEQ ID NO:20) (see, also, FIG. 3).

Also, for example, when one of the cytokines is interleukin-7 (IL-7), at least one of the engineered Fc antibody domains can be C-terminally linked to the N-terminus of the IL-7 (herein referred to as Fc-IL-7) via an engineered metalloprotease-resistant linker sequence. In some embodiments, the engineered metalloprotease-resistant linker sequence can comprise the amino acid sequence SLSPGKDCDIEGK (SEQ ID NO:21) (see, also, FIG. 3).

As an additional example, when one of the cytokines is interleukin-15 (IL-15), at least one of the engineered Fc antibody domains can be C-terminally linked to the N-terminus of the IL-15 (herein referred to as Fc-IL-15) via an engineered metalloprotease-resistant linker sequence. In some embodiments, the engineered metalloprotease-resistant linker sequence can comprise the amino acid sequence SLSPGKN (SEQ ID NO:22) (see, also, FIG. 3).

FIG. 2 also illustrates that the engineered Fc antibody domains can be N-terminally linked to a C-terminus of at least one of the cytokines (which can then be bound to a protein cage polypeptide) to achieve their augmented function of activating and expanding T cells beyond the capabilities of soluble cytokines alone. Table 1 also lists out representative sequences for these Fc-cytokine variants.

For example, when one of the cytokines is interleukin-2 (IL-2), at least one of the engineered Fc antibody domains can be N-terminally linked to the C-terminus of the IL-2 (herein referred to as IL-2-Fc) via an engineered metalloprotease-resistant linker sequence. In some embodiments, the engineered metalloprotease-resistant linker can comprise the amino acid sequence TPKSCDKTHT (SEQ ID NO:23) (see, also, FIG. 3).

Also, for example, when one of the cytokines is interleukin-7 (IL-7), at least one of the engineered Fc antibody domains can be N-terminally linked to the C-terminus of the IL-7 (herein referred to as Fc-IL-7) via an engineered metalloprotease-resistant linker sequence. In some embodiments, the engineered metalloprotease-resistant linker sequence can comprise the amino acid sequence HPKSCDKTHT (SEQ ID NO:24) (see, also, FIG. 3).

As an additional example, when one of the cytokines is interleukin-15 (IL-15), at least one of the engineered Fc antibody domains can be N-terminally linked to the C-terminus of the IL-15 (herein referred to as Fc-IL-15) via an engineered metalloprotease-resistant linker sequence. In some embodiments, the engineered metalloprotease-resistant linker sequence can comprise the amino acid sequence TSPKSCDKTHT (SEQ ID NO:25) (see, also, FIG. 3).

FIG. 2 also illustrates that the CCCs can comprise a signal peptide or leader sequence linked to an N-terminus of at least one of the engineered Fc antibody domains or at least one of the cytokines.

In some embodiments, the signal peptide can be a murine Ig heavy signal peptide for expression in Chinese hamster ovary (CHO) cells. The signal peptide can improve the secretion efficiency of the engineered molecule in CHO cells.

As a more specific example, the signal peptide can comprise the amino acid sequence MGWSCIILFL-VATATGVHS (SEQ ID NO:26).

FIG. 3 illustrates example linker sequences designed to link the Fc and cytokine components of the following CCCs: (1) Fc-IL-2 CCC, (2) IL-2-Fc CCC, (3) Fc-IL-7 CCC, (4) IL-7-Fc CCC, (5) Fc-IL-15 CCC, and (6) IL-15-Fc CCC (see, also, Table 1). The linkers are underlined in FIG. 3.

Also shown in FIG. 3 are various cleavage sites (e.g., for aspartic protease, cysteine protease, metalloprotease, serine protease, and different multiple protease superfamilies). As will be discussed in more detail with respect to Example 3, metalloproteases are known for mediating cell-surface receptor shedding or cleaving the functional domains of receptors and ligands off of the cells. FIG. 3 shows that none of the linkers are cleaved in the middle of the linkers except for serine proteases. Serine proteases are less of a concern since they are often localized inside the cells themselves.

The amino acid sequences shown in FIG. 3 (and listed below) are portions of the amino acid sequences listed in Table 1 above:

```
Portion of Engineered Fc-IL-2:
                                     (SEQ ID NO: 27)
QQGNVFSCSVMHEALHNHYTQKSLSLSPGKAPTSSSTKKTQLQLEHLLL

DLQMILNGINNYKNPKLTRML.

Portion of Engineered IL-2-Fc:
                                     (SEQ ID NO: 28)
WITFCQSIISTLTPKSCDKTHTCPPCPAPELLGGPSVFLFPPKPKDTLM

ISRTP.

Portion of Engineered Fc-IL-7:
                                     (SEQ ID NO: 29)
SRWQQGNVFSCSVMHEALHNHYTQKSLSLSPGKDCDIEGKDGKQYESVL

MVSIDQLLDSMKEIGSNCLNN.

Portion of Engineered IL-7-Fc:
                                     (SEQ ID NO: 30)
DLCFLKRLLQEIKTCWNKILMGTKEHPKSCDKTHTCPPCPAPELLGGPS

VFLFPPKPKDTLMISRTPEVTCVVV.

Portion of Engineered Fc-IL-15:
                                     (SEQ ID NO: 31)
WQQGNVFSCSVMHEALHNHYTQKSLSLSPGKNWVNVISDLKKIEDLIQS

MHIDATLYTESDVHPSCKV.

Portion of Engineered IL-15-Fc:
                                     (SEQ ID NO: 32)
FVHIVQMFINTSPKSCDKTHTCPPCPAPELLGGPSVFLFPPKP.
```

Figure 4:
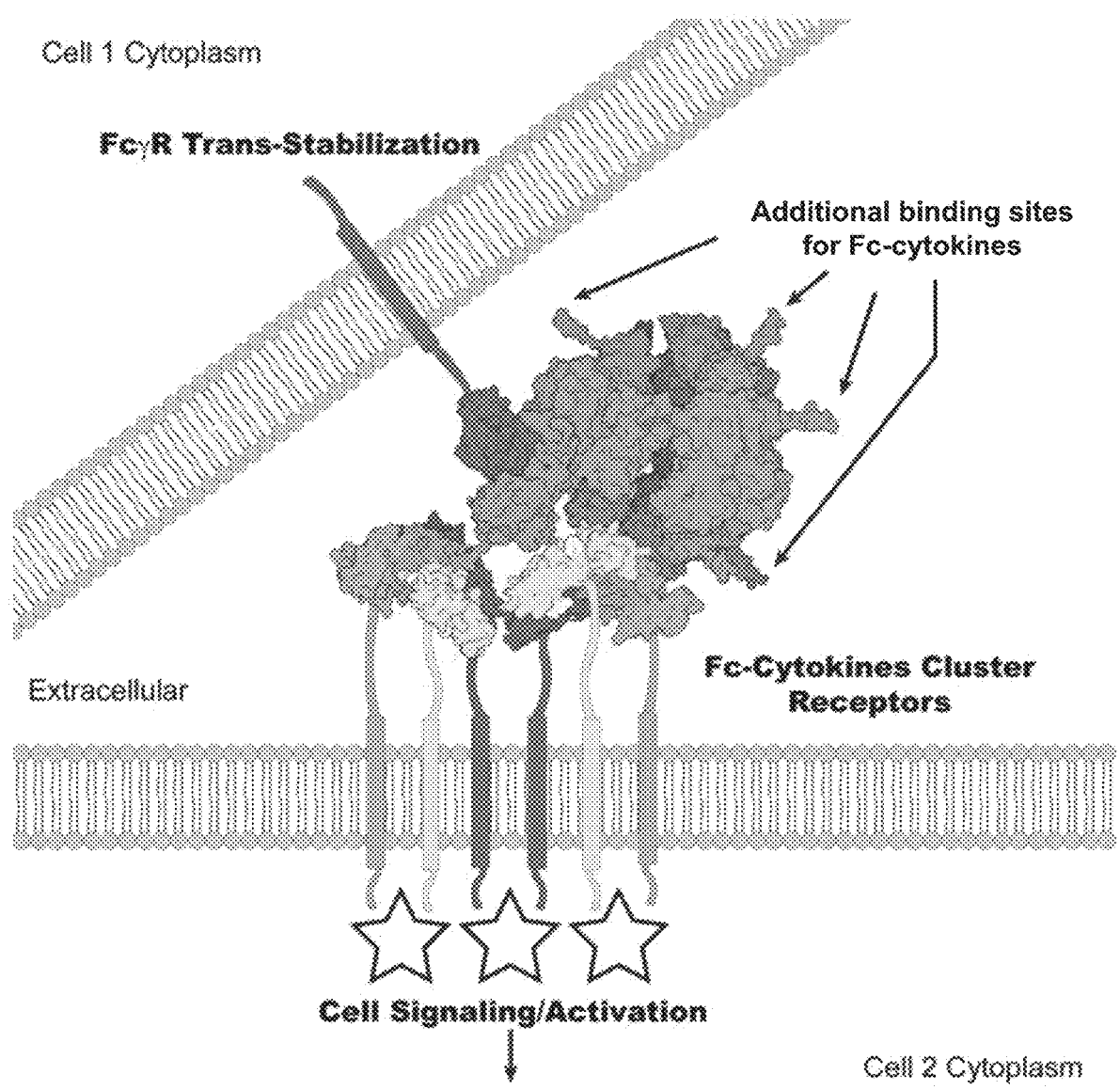
FIG. 4 illustrates an example of an engineered Fc component of the CCC stabilized by an Fcγ receptor (FcγR) of a nearby cell.

FIG. 4 illustrates an example of the engineered Fc component of the CCC stabilized by an Fcγ receptor (FcγR) of a nearby cell. The Fc components of the CCCs can be stabilized via trans-stabilization by nearby cells expressing FcγRs.

In some embodiments, the Fc component of the CCC can be engineered to comprise one or more point mutations to modulate FcγR binding. For example, the Fc component can be engineered to be either FcγR binding competent (i.e., increased affinity for FcγR binding) or FcγR binding incompetent (i.e., decreased affinity for FcγR binding) to avoid antibody-dependent cellular cytotoxicity (ADCC) activation of NK cells.

Three main classes of Fcγ receptors (FcγRs) exist on leukocytes (FcγRI, FcγRII, and FcγRIII) and function in cellular processes such as: ADCC, cytokine release, phagocytosis, and endocytosis [7]. A primary signal to cause NK cells to initiate killing activities, such as release of perforins and granzymes, is ADCC, which requires clustering of FcγRIIIa receptors on the NK cells' surface [8]. Depending on the application, NK cell-mediated ADCC may or may not be desirable.

FIG. 5 illustrates that the Fc component (e.g., human IgG1 Fc) of the CCC can be engineered through mutation of key sites in its FcγR-binding portion. The various ways that the FcγR-binding portion can be modified via point mutations are shown in FIG. 5. Some such point mutations are also discussed in the literature [8, 9, and 10].

In some embodiments, the engineered human IgG1 Fc antibody domain can comprise at least one of the following point mutations relative to SEQ ID NO:1 (see Table 1) to decrease affinity for certain Fcγ receptors (e.g., FcγRIII) and functionally reduce ADCC: P75L, R76W, Y80K, Y80P, Y80R, Y80G, and Y80A.

For example, the Y80K variant can markedly reduce binding to the FcγRIIIa receptor and diminish ADCC. Also, for example, the Y80P variant can markedly reduce binding to FcγRIIIa and cause insufficient N-glycosylation.

As another example, the Y80R variant can markedly reduce binding to the FcγRIIIa receptor. Also, for example, the Y80G variant can markedly reduce binding to the FcγRIIIa receptor. As yet another example, the Y80A variant can markedly reduce binding to the FcγRIIIa receptor and diminish ADCC.

In some embodiments, the engineered human IgG1 Fc antibody domain can comprise at least one of the following point mutations relative to SEQ ID NO:1 (see Table 1) to increase affinity for certain Fcγ receptors and functionally increase ADCC: Y80W.

In some embodiments, the engineered human IgG1 Fc antibody domain can comprise at least one of the following point mutations relative to SEQ ID NO:1 (see Table 1) to decrease affinity for certain Fcγ receptors (e.g., FcγRIIIa) and have a neutral effect on other Fcγ receptors (e.g., FcγRII): S23A, E53A, E77A, Y80F, V87A, A111G, K122A, and D160A.

In some embodiments, the engineered human IgG1 Fc antibody domain can comprise at least one of the following point mutations relative to SEQ ID NO: 1 (see Table 1) to increase affinity for certain Fcγ receptors (e.g., FcγRIIIa) and have a neutral effect on other Fcγ receptors (e.g., FcγRII): E117, K118A, and A123T.

In some embodiments, the engineered human IgG1 Fc antibody domain can comprise at least one of the following point mutations relative to SEQ ID NO: 1 (see Table 1) to increase affinity for certain Fcγ receptors (e.g., FcγRII) and decrease affinity for other Fcγ receptors (e.g., FcγRIIIa): H52A, R85A, and K106A.

In some embodiments, the engineered human IgG1 Fc antibody domain can comprise at least one of the following point mutations relative to SEQ ID NO:1 (see Table 1) to decrease affinity for certain Fcγ receptors (e.g., FcγRII and FcγRIIIa): D54A, Q79A, and A111S.

In some embodiments, the engineered human IgG1 Fc antibody domain can comprise at least one of the following point mutations relative to SEQ ID NO:1 (see Table 1) to increase affinity for certain Fcγ receptors (e.g., FcγRII and FcγRIIIa): T40A and K74A.

As previously discussed, the Fc components of the CCCs can be engineered to be either FcγR binding competent (i.e., increased affinity for FcγR binding) to functionally increase ADCC or FcγR binding incompetent (i.e., decreased affinity for FcγR binding) to functionally decrease ADCC.

EXAMPLES

The examples below are given so as to illustrate the practice of various embodiments of the present disclosure. They are not intended to limit or define the entire scope of this disclosure. It should be appreciated that the disclosure is not limited to the particular embodiments described and illustrated herein but includes all modifications and variations falling within the scope of the disclosure as defined in the appended embodiments.

Example 1: Chimeric Cytokine Complexes (CCCs) Enhance T-Cell Activation and Expansion Beyond Soluble Cytokine Capabilities One unexpected result stemming from the experiments disclosed herein is that CCCs enhance or markedly increase T-cell activation and expansion than equivalent concentrations of soluble cytokines alone or even Fc-cytokines alone.

Human peripheral blood CD3+ T cells were thawed and media exchanged in serum free T-cell expansion medium. T cells were seeded at a concentration of $1 \times 10^6$ cells/mL then placed in a 37° C. and 5% $CO_2$ incubator on day −1. On day 0, cells were activated with an anti-CD3 and anti-CD28 T-cell activation reagent. In some embodiments, the T-cell activation reagent can be a soluble T-cell activator for use in vitro.

In some embodiments, the anti-CD3 and anti-CD28 T-cell activation reagent can comprise a plurality of self-assembling protein nanoparticles decorated with anti-CD3 antibodies and anti-CD28 antibodies. The self-assembling protein nanoparticles can comprise protein cage polypeptides assembled into three-dimensional structures.

In some embodiments, the three-dimensional structure of the protein cage polypeptide can be a tetrahedral pyramid. The protein cage polypeptides can also self-assemble into compact asymmetrical multimeric structures or cage-cage multimers (including dimers).

The three-dimensional structures (e.g., protein cage polypeptide formed into tetrahedral pyramids) can serve as scaffolds for the anti-CD3 antibodies and the anti-CD28 antibodies.

In some embodiments, the protein cage polypeptide can be comprised of a polypeptide comprising an amino acid sequence with at least about 70%, 75%, 80%, 85%, 90%, 95%, 99%, or 100% amino acid identity to the amino acid sequence set forth in any one of SEQ ID NOS: 8-10 (see Table 2).

The protein cage polypeptide can comprise a polypeptide of between about 400 and about 700 amino acid residues in length. In some embodiments, the protein cage polypeptide can comprise a polypeptide of about 450 amino acid residues to about 650 amino acid residues in length.

In some embodiments, the anti-CD3 antibodies can be the "OKT3" clone with multiple host isotypes, such as human, mouse, rabbit, etc. For example, any of the following anti-CD3 antibodies can be used: (i) anti-CD3 monoclonal antibodies (OKT3) distributed by Takara Bio, (ii) GMP monoclonal anti-human CD3 antibodies (OKT3) distributed by ACROBiosystems, (iii) MACS® GMP CD3 pure antibodies distributed by Miltenyi Biotec, or (iv) GMP Ultra-LEAF™ purified anti-human CD3 SF antibodies distributed by BioLegend.

In some embodiments, the anti-CD28 antibodies can be agonist clones with multiple host isotypes, such as human, mouse, rabbit, etc. For example, any of the following anti-CD28 antibodies can be used: (i) anti-CD28 [YTH 913.12] antibodies distributed by Absolute Antibody, (ii) CD28 antibodies, anti-human, clone 15E8 distributed by Miltenyi Biotec, (iii) Ultra-LEAF™ purified anti-human CD28 antibodies, clone cd28.2, distributed by BioLegend, or (iv) BD™ purified mouse anti-human CD28 antibodies, clone L293, distributed by BD Biosciences.

Standard soluble cytokines were added to the medium at concentrations of 10 ng/ml, 15 ng/ml, 20 ng/mL, 25 ng/ml, 30 ng/ml, and 35 ng/ml and CCCs were added to the medium at concentrations equivalent (molar equivalent, m.e.) to those of the standard cytokines. 10 ng/ml of Fc-IL-2s was also added. The CCCs added were FC-IL-2 CCCs. The cytokines added were soluble IL-2s. Cells were then returned to the 37° C. and 5% $CO_2$ incubator.

Figure 6:
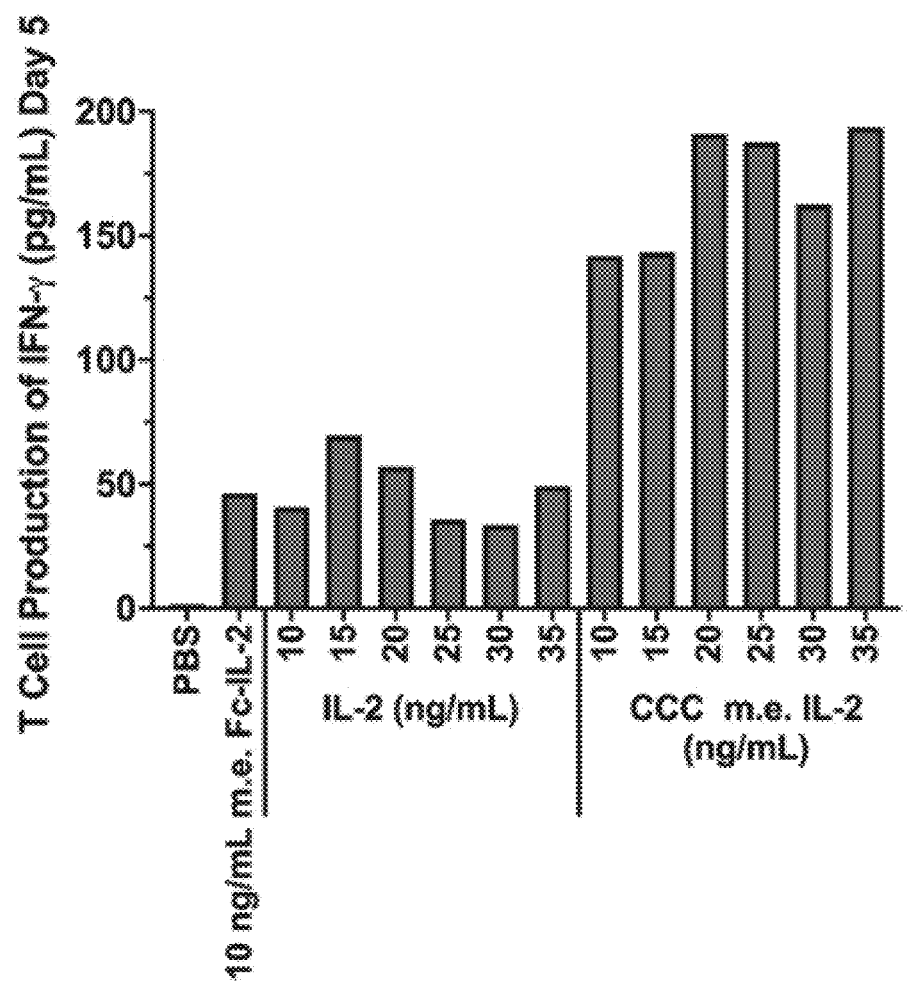
FIG. 6 is a graph illustrating the results of an ELISA specific for detecting IFN-γ produced by T cells. A phosphate buffered saline (PBS) solution was used as the control.

On day 5, medium was collected for an ELISA specific for detecting interferon-gamma (IFN-γ). FIG. 6 is a graph illustrating the results of the ELISA specific for detecting IFN-γ. As shown in FIG. 6, T cells on media supplemented with CCCs (e.g., the FC-IL-2 CCCs) were activated much more than T cells on media supplemented with cytokines (e.g., IL-2s) alone or even Fc-cytokines (e.g., Fc-IL-2s) as indicated by levels of IFN-γ produced by the T cells.

Fresh cell culture medium supplemented with either CCC or standard cytokines was added to the cells at equivalent concentrations (e.g., 10 ng/ml, 15 ng/ml, 20 ng/ml, 25 ng/ml, 30 ng/mL, and 35 ng/ml). Cells were then returned to the 37° C. and 5% $CO_2$ incubator. On day 7, cells were resuspended and collected for flow cytometry.

Figure 7:
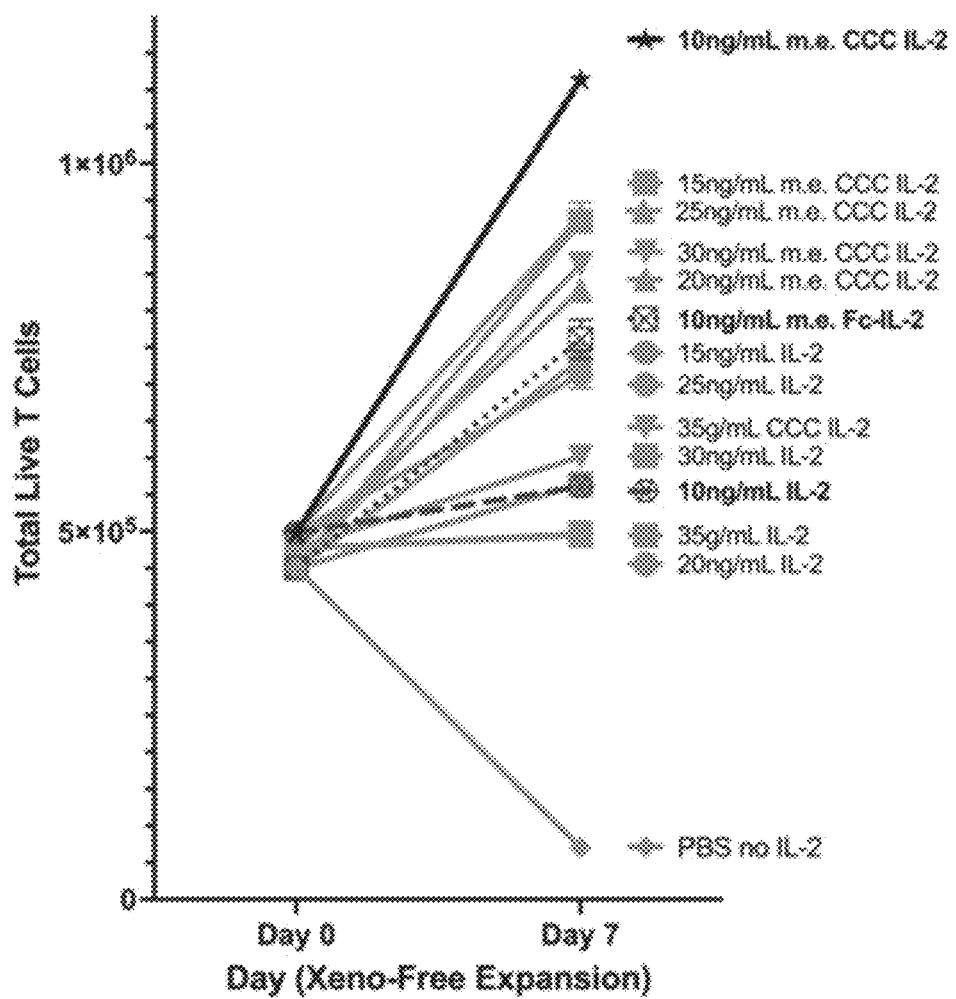
FIG. 7 is a graph illustrating the population of live T cells as determined using flow cytometry on day 7. The T cells were activated and expanded using CCCs, Fc-IL-2s, and IL-2s alone. A phosphate buffered saline (PBS) solution was used as the control.

FIG. 7 is a graph illustrating the population of live T cells as determined using flow cytometry on day 7. Cells were stained with Zombie Aqua to determine the population of live T cells. As shown in FIG. 7, total live T cells on media supplemented with CCCs (e.g., the Fc-IL-2 CCCs) greatly exceeded total live T cells on media supplemented with cytokines (e.g., IL-2s) alone or even Fc-cytokines (e.g., Fc-IL-2s) on day 7.

One unexpected result stemming from the experiments disclosed herein is that CCCs at concentrations between 10 ng/mL and 50 ng/ml of media significantly enhance T-cell expansion than equivalent and even greater concentrations of soluble cytokines (e.g., IL-2s) alone.

Another unexpected result stemming from the experiments disclosed herein is that Fc-cytokine complexes (e.g., Fc-IL-2s) of the type disclosed herein also enhance T-cell expansion than equivalent and even greater concentrations of soluble cytokines (e.g., IL-2s) alone.

Figure 8:
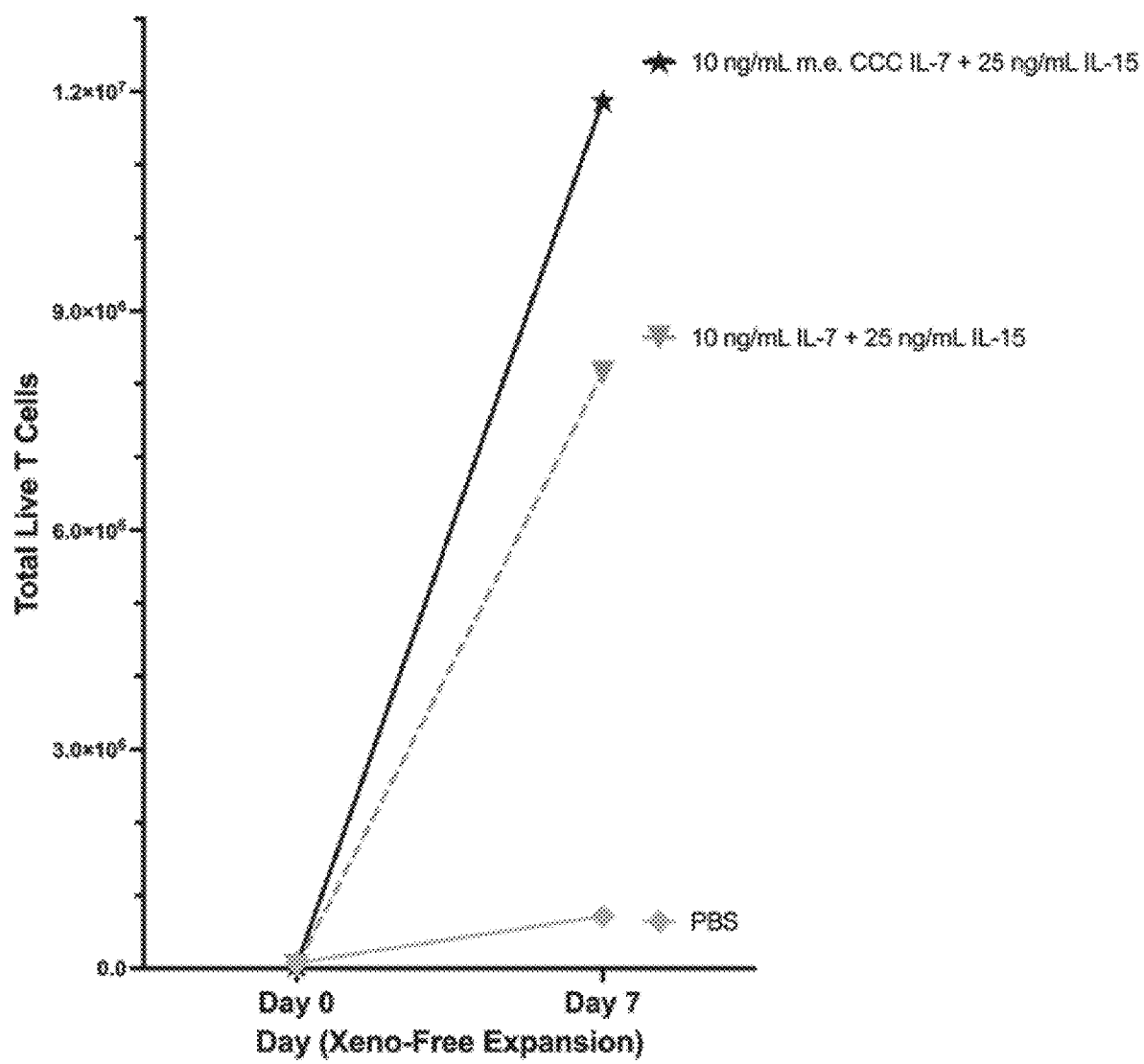
FIG. 8 is a graph illustrating the population of live T cells as determined using flow cytometry on day 7. The T cells were activated and expanded using a combination of CCCs and cytokines and cytokines alone. A phosphate buffered saline (PBS) solution was used as the control.

FIG. 8 is a graph illustrating the population of live T cells as determined using flow cytometry on day 7. Cells were stained with Zombie Aqua to determine the population of live T cells. As shown in FIG. 8, total live T cells on media supplemented with a combination of IL-7-Fc CCCs (i.e., wherein the engineered Fc antibody domain is N-terminally linked to the C-terminus of IL-7 cytokine) and soluble cytokines (e.g., IL-15s) greatly exceeded total live T cells on media supplemented with only soluble cytokines (e.g., IL-7s and IL-15s) on day 7.

Example 2: Chimeric Cytokine Complexes (CCCs) Increase CD4+ T Cell Count in Expanded T Cells Beyond Soluble Cytokine Capabilities Yet another unexpected result stemming from the experiments disclosed herein is that CCCs greatly increase the CD4+ content of the expanded T cells. FIGS. 9A-9C are graphs illustrating the CD4+ T cell count, the CD8+ T cell count, and the total live T cells at day 7, respectively.

Human peripheral blood T cells were thawed and media exchanged in serum free T-cell expansion medium. T cells were seeded at a concentration of $1\times10^6$ cells/mL then placed in a 37° C. and 5% $CO_2$ incubator on day −1. On day 0, cells were activated with an anti-CD3 and anti-CD28 T-cell activation reagent.

In some embodiments, the anti-CD3 and anti-CD28 T-cell activation reagent can comprise a plurality of self-assembling protein nanoparticles decorated with anti-CD3 antibodies and anti-CD28 antibodies. The self-assembling protein nanoparticles can comprise protein cage polypeptides assembled into three-dimensional structures.

In some embodiments, the three-dimensional structure of the protein cage polypeptide can be a tetrahedral pyramid. The protein cage polypeptides can also self-assemble into compact asymmetrical multimeric structures or cage-cage multimers (including dimers).

The three-dimensional structures (e.g., protein cage polypeptide formed into tetrahedral pyramids) can serve as scaffolds for the anti-CD3 antibodies and the anti-CD28 antibodies.

In some embodiments, the protein cage polypeptide can be comprised of a polypeptide comprising an amino acid sequence with at least about 70%, 75%, 80%, 85%, 90%, 95%, 99%, or 100% amino acid identity to the amino acid sequence set forth in any one of SEQ ID NOS: 8-10 (see Table 2).

The protein cage polypeptide can comprise a polypeptide of between about 400 and about 700 amino acid residues in length. In some embodiments, the protein cage polypeptide can comprise a polypeptide of about 450 amino acid residues to about 650 amino acid residues in length.

In some embodiments, the anti-CD3 antibodies can be the "OKT3" clone with multiple host isotypes, such as human, mouse, rabbit, etc. For example, any of the following anti-CD3 antibodies can be used: (i) anti-CD3 monoclonal antibodies (OKT3) distributed by Takara Bio, (ii) GMP monoclonal anti-human CD3 antibodies (OKT3) distributed by ACROBiosystems, (iii) MACS® GMP CD3 pure antibodies distributed by Miltenyi Biotec, or (iv) GMP Ultra-LEAF™ purified anti-human CD3 SF antibodies distributed by BioLegend.

In some embodiments, the anti-CD28 antibodies can be agonist clones with multiple host isotypes, such as human, mouse, rabbit, etc. For example, any of the following anti-CD28 antibodies can be used: (i) anti-CD28 [YTH 913.12] antibodies distributed by Absolute Antibody, (ii) CD28 antibodies, anti-human, clone 15E8 distributed by Miltenyi Biotec, (iii) Ultra-LEAF™ purified anti-human CD28 antibodies, clone cd28.2, distributed by BioLegend, or (iv) BD™ purified mouse anti-human CD28 antibodies, clone L293, distributed by BD Biosciences.

Standard soluble cytokines were added to the medium at a concentration of 20 ng/ml and CCCs were added to the medium at concentrations equivalent (molar equivalent, m.e.) to those of the standard cytokines. The CCCs added were IL-2-Fc CCCs. The cytokines added to compare were soluble IL-2s. On day 7, cells were resuspended and collected for flow cytometry. Cells were stained with Zombie Aqua to determine the population of live cells. The T-cells were then run on the flow cytometer.

Example 3: Cytokine and Chemokine Multiplexing Reveal Increase in Expression of Matrix Metalloproteases (MMPs) by T Cells Human peripheral blood CD3+ T cells were thawed and media exchanged in serum free T-cell expansion medium. T cells were seeded at a concentration of $1\times10^6$ cells/mL in a GREX® 24-well plate then placed in a 37° C. and 5% $CO_2$ incubator on day-1. On day 0, T cells were activated with an anti-CD3 and anti-CD28 T-cell activation reagent.

In some embodiments, the anti-CD3 and anti-CD28 T-cell activation reagent can comprise a plurality of self-assembling protein nanoparticles decorated with anti-CD3 antibodies and anti-CD28 antibodies. The self-assembling protein nanoparticles can comprise protein cage polypeptides assembled into three-dimensional structures.

In some embodiments, the three-dimensional structure of the protein cage polypeptide can be a tetrahedral pyramid. The protein cage polypeptides can also self-assemble into compact asymmetrical multimeric structures or cage-cage multimers (including dimers).

The three-dimensional structures (e.g., protein cage polypeptide formed into tetrahedral pyramids) can serve as scaffolds for the anti-CD3 antibodies and the anti-CD28 antibodies.

In some embodiments, the protein cage polypeptide can be comprised of a polypeptide comprising an amino acid sequence with at least about 70%, 75%, 80%, 85%, 90%, 95%, 99%, or 100% amino acid identity to the amino acid sequence set forth in any one of SEQ ID NOS: 8-10 (see Table 2).

The protein cage polypeptide can comprise a polypeptide of between about 400 and about 700 amino acid residues in length. In some embodiments, the protein cage polypeptide can comprise a polypeptide of about 450 amino acid residues to about 650 amino acid residues in length.

In some embodiments, the anti-CD3 antibodies can be the "OKT3" clone with multiple host isotypes, such as human, mouse, rabbit, etc. For example, any of the following anti-CD3 antibodies can be used: (i) anti-CD3 monoclonal antibodies (OKT3) distributed by Takara Bio, (ii) GMP monoclonal anti-human CD3 antibodies (OKT3) distributed by ACROBiosystems, (iii) MACS® GMP CD3 pure antibodies distributed by Miltenyi Biotec, or (iv) GMP Ultra-LEAF™ purified anti-human CD3 SF antibodies distributed by BioLegend.

In some embodiments, the anti-CD28 antibodies can be agonist clones with multiple host isotypes, such as human, mouse, rabbit, etc. For example, any of the following anti-CD28 antibodies can be used: (i) anti-CD28 [YTH 913.12] antibodies distributed by Absolute Antibody, (ii) CD28 antibodies, anti-human, clone 15E8 distributed by Miltenyi Biotec, (iii) Ultra-LEAF™ purified anti-human CD28 antibodies, clone cd28.2, distributed by BioLegend, or (iv) BD™ purified mouse anti-human CD28 antibodies, clone L293, distributed by BD Biosciences.

Cytokines (e.g., IL-2s) were added to the medium to achieve a final concentration of 10 ng/mL. A 500 µL sample of medium without IL-2 was frozen and was the day 0 control sample. T cells were then returned to the 37° C. and 5% $CO_2$ incubator. On day 3, a 500 µL sample of medium was collected from each sample well and frozen. Fresh culture medium supplemented with IL-2 was then exchanged with spent media such that a final concentration of 10 ng/ml IL-2 was achieved. T cells were then returned to the 37° C. and 5% $CO_2$ incubator. On day 7, a 500 µL sample of medium was collected from each sample well and frozen. Fresh culture medium supplemented with IL-2 was then exchanged with spent media to achieve a final IL-2 concentration of 10 ng/mL. T cells were then returned to the 37° C. and 5% $CO_2$ incubator. The frozen day 0, day 3, and day 7 samples were subjected to a 71-human cytokine/chemokine multiplexing panel that uses a combination of antibody-coupled fluorescent beads to capture analytes and fluorescent detection antibodies to determine the concentration of cytokines and chemokines in the medium.

Figure 10:
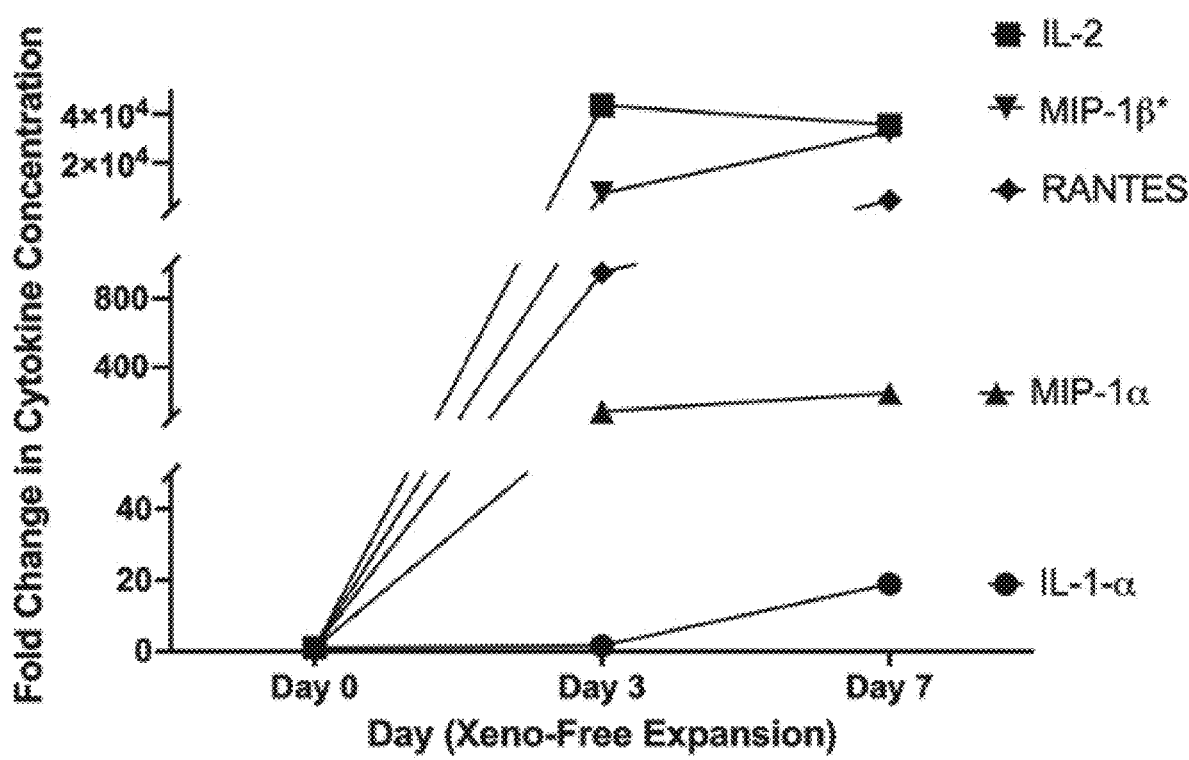
FIG. 10 is a graph showing that upon stimulation with an anti-CD3 and anti-CD28 T-cell activation reagent, peripheral blood donor T cells upregulated the expression of cytokines and chemokines that increase the expression of certain matrix metalloproteases (MMPs) by T cells.

As shown by the graph in FIG. 10, upon stimulation with an anti-CD3 and anti-CD28 T-cell activation reagent, peripheral blood donor T cells upregulated the expression of cytokines and chemokines that increase the expression of matrix metalloproteases (MMPs) (also referred to as matrix metalloproteinases) by T cells.

This is in line with other research which showed that T cells and NK cells express MMPs and the receptor CD100 can be "shed" from the surface through MMP proteolysis activity [11, 12]. Furthermore, it was shown that the chemokines and cytokines, TNF-alpha, IL-1, MIP-1alpha, MIP-1beta, and RANTES upregulated proMMP-9 (the pro-protease prior to enzymatic cleavage into active MMP-9) secretion by $CD3^+$ and $CD4^+$ T cells [13, 14]. Additionally, IL-2 stimulation increases MMP-9 production in T cells [11].

Connecting these lines of research with the pursuit of CCC-based and Fc-cytokine-based cellular agonism, there is a crucial need to protect the chimeric Fc-cytokine linkers of CCCs and Fc-cytokine complexes from metalloprotease enzymes.

Thus, disclosed herein are CCCs and Fc-cytokine complexes with chimeric Fc-cytokine linkers or linker sequences that are protected from metalloprotease enzymes (see FIGS. 2 and 3). Such linkers were designed to not contain any predicted metalloprotease sites. Part of this effort involved using a protease site prediction tool called PROSPER [15].

One technical problem faced by the applicant is how to engineer a metalloprotease-resistant linker that promotes agonism or cell receptor binding. One technical solution discovered and developed by the applicant is to engineer the metalloprotease-resistant linkers such that the linker sequences comprise between 7 to 13 amino acid residues in length. This is supported by the literature which shows an inverse relationship between flexibility and agonism in the case of FcγRs [16]. The applicant predicts a similar relationship with Fc-cytokine chimeras due to a similar type of receptor clustering mechanism involved in both antibody [1] and cytokine agonism [2,3].

In some embodiments, the anti-CD3 and anti-CD28 T-cell activation reagent can comprise a plurality of self-assembling protein nanoparticles decorated with anti-CD3 antibodies and anti-CD28 antibodies. The self-assembling protein nanoparticles can comprise protein cage polypeptides assembled into three-dimensional structures.

In some embodiments, the three-dimensional structure of the protein cage polypeptide can be a tetrahedral pyramid. The protein cage polypeptides can also self-assemble into compact asymmetrical multimeric structures or cage-cage multimers (including dimers).

The three-dimensional structures (e.g., protein cage polypeptide formed into tetrahedral pyramids) can serve as scaffolds for the anti-CD3 antibodies and the anti-CD28 antibodies.

In some embodiments, the protein cage polypeptide can be comprised of a polypeptide comprising an amino acid sequence with at least about 70%, 75%, 80%, 85%, 90%, 95%, 99%, or 100% amino acid identity to the amino acid sequence set forth in any one of SEQ ID NOS: 8-10 (see Table 2).

The protein cage polypeptide can comprise a polypeptide of between about 400 and about 700 amino acid residues in length. In some embodiments, the protein cage polypeptide can comprise a polypeptide of about 450 amino acid residues to about 650 amino acid residues in length.

Example 4: Chimeric Cytokine Complexes (CCCs) Enhance NK Cell Activation and Expansion Another unexpected result stemming from the experiments disclosed herein is that CCCs enhance or markedly increase NK cell activation and expansion when compared to equivalent concentrations of soluble cytokines alone or Fc-cytokines alone.

Human peripheral blood CD56+NK cells were thawed and media exchanged in serum free NK-cell expansion medium on day 0. The medium was supplemented with 10% human platelet lysate and one of the following: (1) standard soluble cytokines (e.g., IL-2s), (2) Fc-cytokine complexes (e.g., IL-2-Fcs), (3) CCCs (e.g., IL-2-Fcs), and (4) CCCs (e.g., IL-2-Fcs) with NK activators. For example, the NK activators can be a soluble NK activator for use in vitro.

NK cells were seeded at a concentration of $7 \times 10^5$ cells/mL then placed in a 37° C. and 5% $CO_2$ incubator. On day 3, the cells were imaged under a light microscope.

Standard soluble cytokines were added to the medium at a concentration of 35 ng/ml and CCCs were added to the medium at concentrations equivalent (molar equivalent, m.e.) to those of the standard cytokines. The CCCs added were IL-2-Fc CCCs.

Figures 11A, 11B, 11C, 11D:
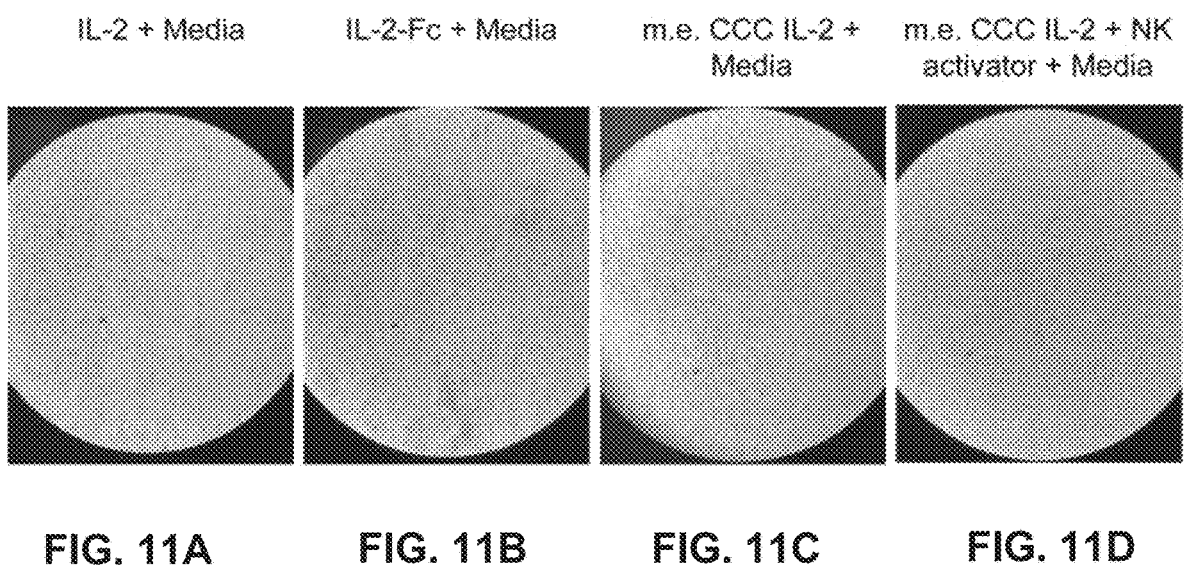
FIGS. 11A-11D illustrate that NK cells on media supplemented with CCCs proliferated much more than NK cells on media supplemented with standard soluble cytokines alone or Fc-cytokines after three days of coincubation.

FIGS. 11A-1D illustrate NK cells imaged under a light microscope. As shown in FIGS. 11A-11D, donor peripheral blood $CD56^+$ NK cells on media supplemented with CCCs (e.g., the IL-2-Fc CCCs and the IL-2-Fc CCCs with NK activators) proliferated much more than NK cells on media supplemented with standard soluble cytokines (e.g., IL-2s) alone or Fc-cytokines alone (e.g., Fc-IL-2s) after three days of coincubation.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit, or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications, and journal articles) are incorporated by reference herein in their entireties except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

The structures in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

All cited references are hereby incorporated by reference in their entireties.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

REFERENCES

[1] Mayes, P. A., Hance, K. W. & Hoos, A. The promise and challenges of immune agonist antibody development in cancer. *Nat. Rev. Drug Discov.* 17, 509-527 (2018).

[2] Spangler, J. B., Moraga, I., Mendoza, J. L. & Garcia, K. C. Insights into cytokine-receptor interactions from cytokine engineering. *Annu. Rev. Immunol.* 33, 139-167 (2015).

[3] Brooks, A. J. et al. Mechanism of activation of protein kinase JAK2 by the growth hormone receptor. *Science* 344, 1249783 (2014).

[4] O'Shea, J. J. & Plenge, R. JAK and STAT signaling molecules in immunoregulation and immune-mediated disease. *Immunity* 36, 542-550 (2012).

[5] Liao, W., Lin, J. X. & Leonard, W. J. Interleukin-2 at the crossroads of effector responses, tolerance, and immunotherapy. *Immunity* 38, 13-25 (2013).

[6] Levin, A. M. et al. Exploiting a natural conformational switch to engineer an interleukin-2 'superkine'. *Nature* 484, 529-533 (2012).

[7] Powell, M. S. & Hogarth, P. M. Fc receptors. *Adv. Exp. Med. Biol.* 640, 22-34 (2008).

[8] de Taeye, S. W. et al. FcgammaR Binding and ADCC Activity of Human IgG Allotypes. *Front. Immunol.* 11, 740 (2020).
[9] Shields, R. L. et al. High resolution mapping of the binding site on human IgG1 for Fc gamma RI, Fc gamma RII, Fc gamma RIII, and FcRn and design of IgG1 variants with improved binding to the Fc gamma R. *J. Biol. Chem.* 276, 6591-6604 (2001).
Isoda, Y. et al. Importance of the Side Chain at Position 296 of Antibody Fc in Interactions with FcgammaRIIIa and Other Fcgamma Receptors. *PLOS One* 10, e0140120 (2015).
Edsparr, K., Basse, P. H., Goldfarb, R. H. & Albertsson, P. Matrix metalloproteinases in cytotoxic lymphocytes impact on tumour infiltration and immunomodulation. *Cancer Microenviron* 4, 351-360 (2011).
Benson, H. L. et al. Endogenous matrix metalloproteinases 2 and 9 regulate activation of CD4+ and CD8+ T cells. *Am J Respir Cell Mol Biol* 44, 700-708 (2011).
Johnatty, R. N. et al. Cytokine and chemokine regulation of proMMP-9 and TIMP-1 production by human peripheral blood lymphocytes. *J. Immunol.* 158, 2327-2333 (1997).
de Almeida, L. G. N. et al. Matrix Metalloproteinases: From Molecular Mechanisms to Physiology, Pathophysiology, and Pharmacology. *Pharmacol. Rev.* 74, 712-768 (2022).
Song, J. et al. PROSPER: an integrated feature-based tool for predicting protease substrate cleavage sites. *PLOS One* 7, e50300 (2012).
Liu, X. et al. Human immunoglobulin G hinge regulates agonistic anti-CD40 immunostimulatory and antitumour activities through biophysical flexibility. *Nature Communications* 10, 4206 (2019).

We claim:

1. A chimeric cytokine complex, comprising:
   a protein cage polypeptide, wherein the protein cage polypeptide comprises polypeptides that self-assemble into a tetrahedral pyramid structure;
   a plurality of engineered Fc antibody domains non-covalently bound to the protein cage polypeptide; and
   one or more cytokines covalently linked to each of the plurality of engineered Fc antibody domains.

2. The chimeric cytokine complex of claim 1, wherein the cytokines are interleukins.

3. The chimeric cytokine complex of claim 2, wherein the interleukins are at least one of interleukin-2s (IL-2s), IL-7s, and IL-15s.

4. A chimeric cytokine complex, comprising:

a protein cage polypeptide;

a plurality of engineered Fc antibody domains non-covalently bound to the protein cage polypeptide, wherein the plurality of engineered Fc antibody domains comprises between six and twelve engineered Fc antibody domains non-covalently bound to the protein cage polypeptide; and one or more cytokines covalently linked to each of the plurality of engineered Fc antibody domains.

5. The chimeric cytokine complex of claim 4, wherein between 12 and 24 cytokines are covalently linked to the plurality of engineered Fc antibody domains in total.

6. A chimeric cytokine complex, comprising:
a protein cage polypeptide;
a plurality of engineered Fc antibody domains non-covalently bound to the protein cage polypeptide; and
one or more cytokines covalently linked to each of the plurality of engineered Fc antibody domains, wherein each of the one or more cytokines is covalently linked to one of the engineered Fc antibody domains via an engineered metalloprotease-resistant linker sequence.

7. The chimeric cytokine complex of claim 6, wherein the engineered metalloprotease-resistant linker sequence is between 7 to 13 amino acid residues in length.

8. The chimeric cytokine complex of claim 1, wherein at least one of the engineered Fc antibody domains is C-terminally covalently linked to an N-terminus of at least one of the cytokines.

9. The chimeric cytokine complex of claim 8, wherein one of the cytokines is interleukin-2 (IL-2), wherein at least one of the engineered Fc antibody domains is covalently linked to the IL-2 via an engineered metalloprotease-resistant linker sequence comprising the amino acid sequence SLSPGKAPTS (SEQ ID NO:20).

10. The chimeric cytokine complex of claim 8, wherein one of the cytokines is interleukin-7 (IL-7), wherein at least one of the engineered Fc antibody domains is covalently linked to the IL-7 via an engineered metalloprotease-resistant linker sequence comprising the amino acid sequence SLSPGKDCDIEGK (SEQ ID NO: 21).

11. The chimeric cytokine complex of claim 8, wherein one of the cytokines is interleukin-15 (IL-15), wherein at least one of the engineered Fc antibody domains is covalently linked to the IL-15 via an engineered metalloprotease-resistant linker sequence comprising the amino acid sequence SLSPGKN (SEQ ID NO:22).

12. The chimeric cytokine complex of claim 1, wherein at least one of the engineered Fc antibody domains is N-terminally covalently linked to a C-terminus of at least one of the cytokines.

13. The chimeric cytokine complex of claim 12, wherein one of the cytokines is interleukin-2 (IL-2), wherein at least one of the engineered Fc antibody domains is covalently linked to the IL-2 via an engineered metalloprotease-resistant linker sequence comprising the amino acid sequence TPKSCDKTHT (SEQ ID NO:23).

14. The chimeric cytokine complex of claim 12, wherein one of the cytokines is interleukin-7 (IL-7), wherein at least one of the engineered Fc antibody domains is covalently linked to the IL-7 via an engineered metalloprotease-resistant linker sequence comprising the amino acid sequence HPKSCDKTHT (SEQ ID NO:24).

15. The chimeric cytokine complex of claim 12, wherein one of the cytokines is interleukin-15 (IL-15), wherein at least one of the engineered Fc antibody domains is covalently linked to the IL-15 via an engineered metalloprotease-resistant linker sequence comprising the amino acid sequence TSPKSCDKTHT (SEQ ID NO:25).

16. The chimeric cytokine complex of claim 1, wherein the engineered Fc antibody domains are engineered human Fc antibody domains.

17. The chimeric cytokine complex of claim 16, wherein the engineered human Fc antibody domains are engineered human IgG1 Fc antibody domains.

18. The chimeric cytokine complex of claim 17, wherein one of the engineered human IgG1 Fc antibody domains comprises an amino acid sequence with at least about 70%, 75%, 80%, 85%, 90%, 95%, 99%, or 100% amino acid identity to the amino acid sequence set forth in SEQ ID NO:1.

19. The chimeric cytokine complex of claim 18, wherein the engineered human IgG1 Fc antibody domain comprises at least one of the following point mutations relative to SEQ ID NO:1 to decrease affinity for certain Fcγ receptors and functionally reduce antibody-dependent cellular cytotoxicity (ADCC): P75L, R76W, Y80K, Y80P, Y80R, Y80G, and Y80A.

20. The chimeric cytokine complex of claim 18, wherein the engineered human IgG1 Fc antibody domain comprises the following point mutation relative to SEQ ID NO: 1 to increase affinity for certain Fcγ receptors and functionally increase antibody-dependent cellular cytotoxicity (ADCC): Y80W.

21. The chimeric cytokine complex of claim 18, wherein the engineered human IgG1 Fc antibody domain comprises at least one of the following point mutations relative to SEQ ID NO: 1 to decrease affinity for certain Fcγ receptors and have a neutral effect on other Fcγ receptors: S23A, E53A, E77A, Y80F, V87A, A111G, K122A, and D160A.

22. The chimeric cytokine complex of claim 18, wherein the engineered human IgG1 Fc antibody domain comprises at least one of the following point mutations relative to SEQ ID NO:1 to increase affinity for certain Fcγ receptors and have a neutral effect on other Fcγ receptors: E117, K118A, and A123T.

23. The chimeric cytokine complex of claim 18, wherein the engineered human IgG1 Fc antibody domain comprises at least one of the following point mutations relative to SEQ ID NO: 1 to increase affinity for certain Fcγ receptors and decrease affinity for certain other Fcγ receptors: H52A, R85A, and K106A.

24. The chimeric cytokine complex of claim 18, wherein the engineered human IgG1 Fc antibody domain comprises at least one of the following point mutations relative to SEQ ID NO: 1 to decrease affinity for certain Fcγ receptors: D54A, Q79A, and A111S.

25. The chimeric cytokine complex of claim 18, wherein the engineered human IgG1 Fc antibody domain comprises at least one of the following point mutations relative to SEQ ID NO:1 to increase affinity for certain Fcγ receptors: T40A and K74A.

26. The chimeric cytokine complex of claim 1, wherein the Fc antibody domains are engineered rabbit Fc antibody domains.

27. The chimeric cytokine complex of claim 1, further comprising a signal peptide linked to an N-terminus of at least one of the engineered Fc antibody domains or at least one of the cytokines.

* * * * *

```
                              SEQUENCE LISTING

Sequence total quantity: 32
SEQ ID NO: 1            moltype = AA  length = 231
FEATURE                 Location/Qualifiers
source                  1..231
                        mol_type = protein
                        organism = synthetic construct
SEQUENCE: 1
PKSCDKTHTC PPCPAPELLG GPSVFLFPPK PKDTLMISRT PEVTCVVVDV SHEDPEVKFN   60
WYVDGVEVHN AKTKPREEQY NSTYRVVSVL TVLHQDWLNG KEYKCKVSNK ALPAPIEKTI  120
SKAKGQPREP QVYTLPPSRD ELTKNQVSLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 2            moltype = AA  length = 383
FEATURE                 Location/Qualifiers
source                  1..383
                        mol_type = protein
                        organism = synthetic construct
SEQUENCE: 2
MGWSCIILFL VATATGVHSP KSCDKTHTCP PCPAPELLGG PSVFLFPPKP KDTLMISRTP   60
EVTCVVVDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSRDE LTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK APTSSSTKKT QLQLEHLLLD LQMILNGINN YKNPKLTRML TFKFYMPKKA  300
TELKHLQCLE EELKPLEEVL NLAQSKNFHL RPRDLISNIN VIVLELKGSE TTFMCEYADE  360
TATIVEFLNR WITFCQSIIS TLT                                          383

SEQ ID NO: 3            moltype = AA  length = 383
FEATURE                 Location/Qualifiers
source                  1..383
                        mol_type = protein
                        organism = synthetic construct
SEQUENCE: 3
MGWSCIILFL VATATGVHSA PTSSSTKKTQ LQLEHLLLDL QMILNGINNY KNPKLTRMLT   60
FKFYMPKKAT ELKHLQCLEE ELKPLEEVLN LAQSKNFHLR PRDLISNINV IVLELKGSET  120
TFMCEYADET ATIVEFLNRW ITFCQSIIST LTPKSCDKTH TCPPCPAPEL LGGPSVFLFP  180
PKPKDTLMIS RTPEVTCVVV DVSHEDPEVK FNWYVDGVEV HNAKTKPREE QYNSTYRVVS  240
VLTVLHQDWL NGKEYKCKVS NKALPAPIEK TISKAKGQPR EPQVYTLPPS RDELTKNQVS  300
LTCLVKGFYP SDIAVEWESN GQPENNYKTT PPVLDSDGSF FLYSKLTVDK SRWQQGNVFS  360
CSVMHEALHN HYTQKSLSLS PGK                                          383

SEQ ID NO: 4            moltype = AA  length = 402
FEATURE                 Location/Qualifiers
source                  1..402
                        mol_type = protein
                        organism = synthetic construct
SEQUENCE: 4
MGWSCIILFL VATATGVHSP KSCDKTHTCP PCPAPELLGG PSVFLFPPKP KDTLMISRTP   60
EVTCVVVDVS HEDPEVKFNW YVDGVEVHNA KTKPREEQYN STYRVVSVLT VLHQDWLNGK  120
EYKCKVSNKA LPAPIEKTIS KAKGQPREPQ VYTLPPSRDE LTKNQVSLTC LVKGFYPSDI  180
AVEWESNGQP ENNYKTTPPV LDSDGSFFLY SKLTVDKSRW QQGNVFSCSV MHEALHNHYT  240
QKSLSLSPGK DCDIEGKDGK QYESVLMVSI DQLLDSMKEI GSNCLNNEFN FFKRHICDAN  300
KEGMFLFRAA RKLRQFLKMN STGDFDLHLL KVSEGTTILL NCTGQVKGRK PAALGEAQPT  360
KSLEENKSLK EQKKLNDLCF LKRLLQEIKT CWNKILMGTK EH                     402

SEQ ID NO: 5            moltype = AA  length = 402
FEATURE                 Location/Qualifiers
source                  1..402
```

```
                           mol_type = protein
                           organism = synthetic construct
SEQUENCE: 5
MGWSCIILFL  VATATGVHSD  CDIEGKDGKQ  YESVLMVSID  QLLDSMKEIG  SNCLNNEFNF   60
FKRHICDANK  EGMFLFRAAR  KLRQFLKMNS  TGDFDLHLLK  VSEGTTILLN  CTGQVKGRKP  120
AALGEAQPTK  SLEENKSLKE  QKKLNDLCFL  KRLLQEIKTC  WNKILMGTKE  HPKSCDKTHT  180
CPPCPAPELL  GGPSVFLFPP  KPKDTLMISR  TPEVTCVVVD  VSHEDPEVKF  NWYVDGVEVH  240
NAKTKPREEQ  YNSTYRVVSV  LTVLHQDWLN  GKEYKCKVSN  KALPAPIEKT  ISKAKGQPRE  300
PQVYTLPPSR  DELTKNQVSL  TCLVKGFYPS  DIAVEWESNG  QPENNYKTTP  PVLDSDGSFF  360
LYSKLTVDKS  RWQQGNVFSC  SVMHEALHNH  YTQKSLSLSP  GK                      402

SEQ ID NO: 6               moltype = AA  length = 364
FEATURE                    Location/Qualifiers
source                     1..364
                           mol_type = protein
                           organism = synthetic construct
SEQUENCE: 6
MGWSCIILFL  VATATGVHSP  KSCDKTHTCP  PCPAPELLGG  PSVFLFPPKP  KDTLMISRTP   60
EVTCVVVDVS  HEDPEVKFNW  YVDGVEVHNA  KTKPREEQYN  STYRVVSVLT  VLHQDWLNGK  120
EYKCKVSNKA  LPAPIEKTIS  KAKGQPREPQ  VYTLPPSRDE  LTKNQVSLTC  LVKGFYPSDI  180
AVEWESNGQP  ENNYKTTPPV  LDSDGSFFLY  SKLTVDKSRW  QQGNVFSCSV  MHEALHNHYT  240
QKSLSLSPGK  NWVNVISDLK  KIEDLIQSMH  IDATLYTESD  VHPSCKVTAM  KCFLLELQVI  300
SLESGDASIH  DTVENLIILA  NNSLSSNGNV  TESGCKECEE  LEEKNIKEFL  QSFVHIVQMF  360
INTS                                                                   364

SEQ ID NO: 7               moltype = AA  length = 364
FEATURE                    Location/Qualifiers
source                     1..364
                           mol_type = protein
                           organism = synthetic construct
SEQUENCE: 7
MGWSCIILFL  VATATGVHSN  WVNVISDLKK  IEDLIQSMHI  DATLYTESDV  HPSCKVTAMK   60
CFLLELQVIS  LESGDASIHD  TVENLIILAN  NSLSSNGNVT  ESGCKECEEL  EEKNIKEFLQ  120
SFVHIVQMFI  NTSPKSCDKT  HTCPPCPAPE  LLGGPSVFLF  PPKPKDTLMI  SRTPEVTCVV  180
VDVSHEDPEV  KFNWYVDGVE  VHNAKTKPRE  EQYNSTYRVV  SVLTVLHQDW  LNGKEYKCKV  240
SNKALPAPIE  KTISKAKGQP  REPQVYTLPP  SRDELTKNQV  SLTCLVKGFY  PSDIAVEWES  300
NGQPENNYKT  TPPVLDSDGS  FFLYSKLTVD  KSRWQQGNVF  SCSVMHEALH  NHYTQKSLSL  360
SPGK                                                                   364

SEQ ID NO: 8               moltype = AA  length = 478
FEATURE                    Location/Qualifiers
source                     1..478
                           mol_type = protein
                           organism = synthetic construct
SEQUENCE: 8
MPFITVGQEN  STSIDLYYED  HGTGTPVVLI  HGFPLSGHSW  ERQSAALLDA  GYRVITYDRR   60
GFGQSSQPTT  GYDYDTFAAD  LNTVLETLDL  QDAVLVGFSM  GTGEVARYVS  SYGTARIAAV  120
AFLASLEPFL  LKTDDNPDGA  APQEFFDGIV  AAVKADRYAF  YTGFFNDFYN  LDENLGTRIS  180
EEAVRNSWNT  AASGGFFAAA  AAPTTWYTDF  RADIPRIDVP  ALILHGTGDR  TLPIENTARV  240
FHKALPSAEY  VEVEGAPHGL  LWTHAEEVNT  ALLAFLAKAQ  EAQKQLLTE   VETYVLSIIP  300
SGPLKAEIAQ  RLEDVFAGRW  GSGADCAWHL  GELVWCTAGS  GWEDLEVLME  WLKTRPILSP  360
LTKGILGFVF  TLTVPSERGL  QRRRFVQNAL  NGNGDPNNMD  KAVKLYRKLK  REITFHGAKE  420
ISLSYSAGAL  ASCMGLIYNR  MGAVTTEVAF  GLVCATCEQI  ADSQHRSHRQ  LEHHHHHH    478

SEQ ID NO: 9               moltype = AA  length = 478
FEATURE                    Location/Qualifiers
source                     1..478
                           mol_type = protein
                           organism = synthetic construct
SEQUENCE: 9
MPFITVGQEN  STSIDLYYED  HGTGTPVVLI  HGFPLSGHSW  ERQSAALLDA  GYRVITYDRR   60
GFGQSSQPTT  GYDYDTFAAD  LNTVLETLDL  QDAVLVGFSM  GTGEVARYVS  SYGTARIAAV  120
AFLASLEPFL  LKTDDNPDGA  APQEFFDGIV  AAVKADRYAF  YTGFFNDFYN  LDENLGTRIS  180
EEAVRNSWNT  AASGGFFAAA  AAPTTWYTDF  RADIPRIDVP  ALILHGTGDR  TLPIENTARV  240
FHKALPSAEY  VEVEGAPHGL  LWTHAEEVNT  ALLAFLAKAQ  EAQKQLLTE   VETYVLSIIP  300
SGPLKAEIAQ  RLEDVFAGGG  RWGADCAWHL  GELVWCTAGW  EGGDLEVLME  WLKTRPILSP  360
LTKGILGFVF  TLTVPSERGL  QRRRFVQNAL  NGNGDPNNMD  KAVKLYRKLK  REITFHGAKE  420
ISLSYSAGAL  ASCMGLIYNR  MGAVTTEVAF  GLVCATCEQI  ADSQHRSHRQ  LEHHHHHH    478

SEQ ID NO: 10              moltype = AA  length = 470
FEATURE                    Location/Qualifiers
source                     1..470
                           mol_type = protein
                           organism = synthetic construct
SEQUENCE: 10
MPFITVGQEN  STSIDLYYED  HGTGTPVVLI  HGFPLSGHSW  ERQSAALLDA  GYRVITYDRR   60
GFGQSSQPTT  GYDYDTFAAD  LNTVLETLDL  QDAVLVGFSM  GTGEVARYVS  SYGTARIAAV  120
AFLASLEPFL  LKTDDNPDGA  APQEFFDGIV  AAVKADRYAF  YTGFFNDFYN  LDENLGTRIS  180
EEAVRNSWNT  AASGGFFAAA  AAPTTWYTDF  RADIPRIDVP  ALILHGTGDR  TLPIENTARV  240
```

```
FHKALPSAEY VEVEGAPHGL LWTHAEEVNT ALLAFLAKAQ EAQKQKLLTE VETYVLSIIP    300
SGPLKAEIAQ RLEDVFAGGA DCAWHLGELV WCTAGDLEVL MEWLKTRPIL SPLTKGILGF    360
VFTLTVPSER GLQRRRFVQN ALNGNGDPNN MDKAVKLYRK LKREITFHGA KEISLSYSAG    420
ALASCMGLIY NRMGAVTTEV AFGLVCATCE QIADSQHRSH RQLEHHHHHH               470

SEQ ID NO: 11           moltype = AA   length = 478
FEATURE                 Location/Qualifiers
source                  1..478
                        mol_type = protein
                        organism = synthetic construct
SEQUENCE: 11
MPFITVGQEN STSIDLYYED HGTGTPVVLI HGFPLSGHSW ERQSAALLDA GYRVITYDRR    60
GFGQSSQPTT GYDYDTFAAD LNTVLETLDL QDAVLVGFSM GTGEVARYVS SYGTARIAAV   120
AFLASLEPFL LKTDDNPDGA APQEFFDGIV AAVKADRYAF YTGFFNDFYN LDENLGTRIS   180
EEAVRNSWNT AASGGFFAAA AAPTTWYTDF RADIPRIDVP ALILHGTGDR TLPIENTARV   240
FHKALPSAEY VEVEGAPHGL LWTHAEEVNT ALLAFLAKAQ EAQKQKLLTE VETYVLSIIP   300
SGPLKAEIAQ RLEDVFAGRW GSGCDCAWHL GELVWCTCGS GWEDLEVLME WLKTRPILSP   360
LTKGILGFVF TLTVPSERGL QRRRFVQNAL NGNGDPNNMD KAVKLYRKLK REITFHGAKE   420
ISLSYSAGAL ASCMGLIYNR MGAVTTEVAF GLVCATCEQI ADSQHRSHRQ LEHHHHHH     478

SEQ ID NO: 12           moltype = AA   length = 478
FEATURE                 Location/Qualifiers
source                  1..478
                        mol_type = protein
                        organism = synthetic construct
SEQUENCE: 12
MPFITVGQEN STSIDLYYED HGTGTPVVLI HGFPLSGHSW ERQSAALLDA GYRVITYDRR    60
GFGQSSQPTT GYDYDTFAAD LNTVLETLDL QDAVLVGFSM GTGEVARYVS SYGTARIAAV   120
AFLASLEPFL LKTDDNPDGA APQEFFDGIV AAVKADRYAF YTGFFNDFYN LDENLGTRIS   180
EEAVRNSWNT AASGGFFAAA AAPTTWYTDF RADIPRIDVP ALILHGTGDR TLPIENTARV   240
FHKALPSAEY VEVEGAPHGL LWTHAEEVNT ALLAFLAKAQ EAQKQKLLTE VETAVLSIIP   300
SGPLKAEIAQ RLEDVFAGRW GSGADCAWHL GELVWCTAGS GWEDLEVLME WLKTRPILSP   360
LTKGILGFVF TLTVPSERGL QRRRFVQNAL NGNGDPNNMD KAVKLYRKLK REITFHGAKE   420
ISLSYSAGAL ASCMGLIYNR MGAVTTEVAF GLVCATCEQI ADSQHRSHRQ LEHHHHHH     478

SEQ ID NO: 13           moltype = AA   length = 478
FEATURE                 Location/Qualifiers
source                  1..478
                        mol_type = protein
                        organism = synthetic construct
SEQUENCE: 13
MPFITVGQEN STSIDLYYED HGTGTPVVLI HGFPLSGHSW ERQSAALLDA GYRVITYDRR    60
GFGQSSQPTT GYDYDTFAAD LNTVLETLDL QDAVLVGFSM GTGEVARYVS SYGTARIAAV   120
AFLASLEPFL LKTDDNPDGA APQEFFDGIV AAVKADRYAF YTGFFNDFYN LDENLGTRIS   180
EEAVRNSWNT AASGGFFAAA AAPTTWYTDF RADIPRIDVP ALILHGTGDR TLPIENTARV   240
FHKALPSAEY VEVEGAPHGL LWTHAEEVNT ALLAFLAKAQ EAQKQKLLTE VETAVLSIIP   300
SGPLKAEIAQ RLEDVFAGGG RWGADCAWHL GELVWCTGEG EGGDLEVLME WLKTRPILSP   360
LTKGILGFVF TLTVPSERGL QRRRFVQNAL NGNGDPNNMD KAVKLYRKLK REITFHGAKE   420
ISLSYSAGAL ASCMGLIYNR MGAVTTEVAF GLVCATCEQI ADSQHRSHRQ LEHHHHHH     478

SEQ ID NO: 14           moltype = AA   length = 470
FEATURE                 Location/Qualifiers
source                  1..470
                        mol_type = protein
                        organism = synthetic construct
SEQUENCE: 14
MPFITVGQEN STSIDLYYED HGTGTPVVLI HGFPLSGHSW ERQSAALLDA GYRVITYDRR    60
GFGQSSQPTT GYDYDTFAAD LNTVLETLDL QDAVLVGFSM GTGEVARYVS SYGTARIAAV   120
AFLASLEPFL LKTDDNPDGA APQEFFDGIV AAVKADRYAF YTGFFNDFYN LDENLGTRIS   180
EEAVRNSWNT AASGGFFAAA AAPTTWYTDF RADIPRIDVP ALILHGTGDR TLPIENTARV   240
FHKALPSAEY VEVEGAPHGL LWTHAEEVNT ALLAFLAKAQ EAQKQKLLTE VETAVLSIIP   300
SGPLKAEIAQ RLEDVFAGGA DCAWHLGELV WCTAGDLEVL MEWLKTRPIL SPLTKGILGF   360
VFTLTVPSER GLQRRRFVQN ALNGNGDPNN MDKAVKLYRK LKREITFHGA KEISLSYSAG   420
ALASCMGLIY NRMGAVTTEV AFGLVCATCE QIADSQHRSH RQLEHHHHHH               470

SEQ ID NO: 15           moltype = AA   length = 478
FEATURE                 Location/Qualifiers
source                  1..478
                        mol_type = protein
                        organism = synthetic construct
SEQUENCE: 15
MPFITVGQEN STSIDLYYED HGTGTPVVLI HGFPLSGHSW ERQSAALLDA GYRVITYDRR    60
GFGQSSQPTT GYDYDTFAAD LNTVLETLDL QDAVLVGFSM GTGEVARYVS SYGTARIAAV   120
AFLASLEPFL LKTDDNPDGA APQEFFDGIV AAVKADRYAF YTGFFNDFYN LDENLGTRIS   180
EEAVRNSWNT AASGGFFAAA AAPTTWYTDF RADIPRIDVP ALILHGTGDR TLPIENTARV   240
FHKALPSAEY VEVEGAPHGL LWTHAEEVNT ALLAFLAKAQ EAQKQKLLTE VETAVLSIIP   300
SGPLKAEIAQ RLEDVFAGRW GSGCDCAWHL GELVWCTCGS GWEDLEVLME WLKTRPILSP   360
LTKGILGFVF TLTVPSERGL QRRRFVQNAL NGNGDPNNMD KAVKLYRKLK REITFHGAKE   420
ISLSYSAGAL ASCMGLIYNR MGAVTTEVAF GLVCATCEQI ADSQHRSHRQ LEHHHHHH     478
```

```
SEQ ID NO: 16          moltype = AA   length = 25
FEATURE                Location/Qualifiers
source                 1..25
                       mol_type = protein
                       organism = synthetic construct
SEQUENCE: 16
RWGSGADCAW HLGELVWCTA GSGWE                                         25

SEQ ID NO: 17          moltype = AA   length = 25
FEATURE                Location/Qualifiers
source                 1..25
                       mol_type = protein
                       organism = synthetic construct
SEQUENCE: 17
GGRWGADCAW HLGELVWCTA GWEGG                                         25

SEQ ID NO: 18          moltype = AA   length = 17
FEATURE                Location/Qualifiers
source                 1..17
                       mol_type = protein
                       organism = synthetic construct
SEQUENCE: 18
GADCAWHLGE LVWCTAG                                                  17

SEQ ID NO: 19          moltype = AA   length = 25
FEATURE                Location/Qualifiers
source                 1..25
                       mol_type = protein
                       organism = synthetic construct
SEQUENCE: 19
RWGSGCDCAW HLGELVWCTC GSGWE                                         25

SEQ ID NO: 20          moltype = AA   length = 10
FEATURE                Location/Qualifiers
source                 1..10
                       mol_type = protein
                       organism = synthetic construct
SEQUENCE: 20
SLSPGKAPTS                                                          10

SEQ ID NO: 21          moltype = AA   length = 13
FEATURE                Location/Qualifiers
source                 1..13
                       mol_type = protein
                       organism = synthetic construct
SEQUENCE: 21
SLSPGKDCDI EGK                                                      13

SEQ ID NO: 22          moltype = AA   length = 7
FEATURE                Location/Qualifiers
source                 1..7
                       mol_type = protein
                       organism = synthetic construct
SEQUENCE: 22
SLSPGKN                                                             7

SEQ ID NO: 23          moltype = AA   length = 10
FEATURE                Location/Qualifiers
source                 1..10
                       mol_type = protein
                       organism = synthetic construct
SEQUENCE: 23
TPKSCDKTHT                                                          10

SEQ ID NO: 24          moltype = AA   length = 10
FEATURE                Location/Qualifiers
source                 1..10
                       mol_type = protein
                       organism = synthetic construct
SEQUENCE: 24
HPKSCDKTHT                                                          10

SEQ ID NO: 25          moltype = AA   length = 11
FEATURE                Location/Qualifiers
source                 1..11
                       mol_type = protein
                       organism = synthetic construct
SEQUENCE: 25
```

```
TSPKSCDKTH T                                                               11

SEQ ID NO: 26           moltype = AA  length = 19
FEATURE                 Location/Qualifiers
source                  1..19
                        mol_type = protein
                        organism = synthetic construct
SEQUENCE: 26
MGWSCIILFL VATATGVHS                                                       19

SEQ ID NO: 27           moltype = AA  length = 70
FEATURE                 Location/Qualifiers
source                  1..70
                        mol_type = protein
                        organism = synthetic construct
SEQUENCE: 27
QQGNVFSCSV MHEALHNHYT QKSLSLSPGK APTSSSTKKT QLQLEHLLLD LQMILNGINN          60
YKNPKLTRML                                                                 70

SEQ ID NO: 28           moltype = AA  length = 54
FEATURE                 Location/Qualifiers
source                  1..54
                        mol_type = protein
                        organism = synthetic construct
SEQUENCE: 28
WITFCQSIIS TLTPKSCDKT HTCPPCPAPE LLGGPSVFLF PPKPKDTLMI SRTP                54

SEQ ID NO: 29           moltype = AA  length = 70
FEATURE                 Location/Qualifiers
source                  1..70
                        mol_type = protein
                        organism = synthetic construct
SEQUENCE: 29
SRWQQGNVFS CSVMHEALHN HYTQKSLSLS PGKDCDIEGK DGKQYESVLM VSIDQLLDSM          60
KEIGSNCLNN                                                                 70

SEQ ID NO: 30           moltype = AA  length = 74
FEATURE                 Location/Qualifiers
source                  1..74
                        mol_type = protein
                        organism = synthetic construct
SEQUENCE: 30
DLCFLKRLLQ EIKTCWNKIL MGTKEHPKSC DKTHTCPPCP APELLGGPSV FLFPPKPKDT          60
LMISRTPEVT CVVV                                                            74

SEQ ID NO: 31           moltype = AA  length = 68
FEATURE                 Location/Qualifiers
source                  1..68
                        mol_type = protein
                        organism = synthetic construct
SEQUENCE: 31
WQQGNVFSCS VMHEALHNHY TQKSLSLSPG KNWVNVISDL KKIEDLIQSM HIDATLYTES          60
DVHPSCKV                                                                   68

SEQ ID NO: 32           moltype = AA  length = 43
FEATURE                 Location/Qualifiers
source                  1..43
                        mol_type = protein
                        organism = synthetic construct
SEQUENCE: 32
FVHIVQMFIN TSPKSCDKTH TCPPCPAPEL LGGPSVFLFP PKP                            43
```